(12) United States Patent
Niese et al.

(10) Patent No.: US 9,265,600 B2
(45) Date of Patent: Feb. 23, 2016

(54) GRAFT FIXATION

(71) Applicant: ORTHOPEDIATRICS CORP., Warsaw, IN (US)

(72) Inventors: Brad Anthony Niese, Chandler, AZ (US); Eric Wall, Cincinnati, OH (US); Yi-Meng Yen, Wellesley, MA (US); Jeffery D. Arnett, Gilbert, AZ (US); Allen F. Anderson, Nashville, TN (US); Mininder Kocher, Dover, MA (US); Theodore J. Ganley, Bryn Mawr, PA (US); Rebekah Koch, Zionsville, IN (US); Dylan Matthew Hushka, Niwot, CO (US); Ryan Harper, Leesburg, IN (US)

(73) Assignee: ORTHOPEDIATRICS CORP., Warsaw, IN (US)

( * ) Notice: Subject to any disclaimer, the term of this patent is extended or adjusted under 35 U.S.C. 154(b) by 0 days.

(21) Appl. No.: 14/192,128

(22) Filed: Feb. 27, 2014

(65) Prior Publication Data
US 2014/0358230 A1    Dec. 4, 2014

Related U.S. Application Data

(60) Provisional application No. 61/770,000, filed on Feb. 27, 2013.

(51) Int. Cl.
*A61B 17/04* (2006.01)
*A61F 2/08* (2006.01)
*A61B 17/86* (2006.01)

(52) U.S. Cl.
CPC .............. *A61F 2/0811* (2013.01); *A61B 17/04* (2013.01); *A61B 17/0401* (2013.01); *A61B 17/86* (2013.01);

(Continued)

(58) Field of Classification Search
CPC .... A61B 17/04; A61B 17/1146; A61B 17/11; A61B 17/1114; A61B 17/1128; A61F 2/0811; A61F 2/0805; A61F 2002/0817; A61F 2002/0811; A61F 2002/0823; A61F 2002/0847; A61F 2002/0858; A61F 2002/0864; A61F 2002/0835; A61F 2002/0882; A61F 2002/0852
USPC ............... 623/13.11–13.2; 606/232, 233, 228
See application file for complete search history.

(56) References Cited

U.S. PATENT DOCUMENTS

| | | |
|---|---|---|
| 170,144 A | 11/1875 | Williams |
| 4,708,132 A | 11/1987 | Silvestrini |

(Continued)

FOREIGN PATENT DOCUMENTS

| | | |
|---|---|---|
| EP | 1568327 | 8/2005 |
| EP | 1645247 | 4/2006 |

(Continued)

*Primary Examiner* — Alvin Stewart
(74) *Attorney, Agent, or Firm* — Maywood IP Law; G. Jo Hays; David W. Meibos

(57) ABSTRACT

A system for graft fixation including ACL graft reconstruction and fixation is presented. The system may comprise a loop fixation device for retaining a tissue graft. The loop fixation device may comprise a graft retention portion and a cortical fixation portion to allow the loop fixation device to rest on the cortical portion of a bone. A tissue graft may pass through a bone tunnel and engage the loop fixation device preventing withdraw of the tissue graft back through the bone tunnel. The system may also include graft fixation within a bone tunnel using a sleeve, or tube construct, with a fixation member, or screw, to engage a tissue graft within the sleeve.

20 Claims, 41 Drawing Sheets

(52) U.S. Cl.
CPC ... *A61B 2017/044* (2013.01); *A61B 2017/0409* (2013.01); *A61B 2017/0414* (2013.01); *A61B 2017/0445* (2013.01); *A61F 2002/0823* (2013.01); *A61F 2002/0835* (2013.01); *A61F 2002/0852* (2013.01); *A61F 2002/0864* (2013.01); *A61F 2002/0882* (2013.01)

(56) References Cited

U.S. PATENT DOCUMENTS

| | | | |
|---|---|---|---|
| 4,716,893 A | 1/1988 | Fischer | |
| 4,744,793 A * | 5/1988 | Parr et al. | 623/13.14 |
| 4,870,957 A | 10/1989 | Goble | |
| 4,941,466 A | 7/1990 | Romano | |
| 4,997,433 A | 3/1991 | Goble | |
| 5,067,962 A | 11/1991 | Campbell | |
| 5,102,414 A | 4/1992 | Kirsch | |
| 5,108,431 A | 4/1992 | Mansat | |
| 5,108,433 A | 4/1992 | May | |
| 5,176,682 A | 1/1993 | Chow | |
| 5,269,809 A * | 12/1993 | Hayhurst et al. | 606/232 |
| 5,306,290 A | 4/1994 | Martins | |
| 5,306,301 A * | 4/1994 | Graf et al. | 606/232 |
| 5,356,435 A | 10/1994 | Thein | |
| 5,374,269 A | 12/1994 | Rosenberg | |
| 5,425,733 A | 6/1995 | Schmieding | |
| 5,425,767 A * | 6/1995 | Steininger et al. | 623/13.14 |
| 5,431,651 A | 7/1995 | Goble | |
| 5,458,601 A | 10/1995 | Young, Jr. | |
| 5,464,424 A * | 11/1995 | O'Donnell, Jr. | 606/228 |
| 5,545,178 A * | 8/1996 | Kensey et al. | 606/232 |
| 5,562,669 A * | 10/1996 | McGuire | 623/13.12 |
| 5,618,314 A * | 4/1997 | Harwin et al. | 606/232 |
| 5,702,397 A * | 12/1997 | Goble et al. | 606/232 |
| 5,733,307 A * | 3/1998 | Dinsdale | 606/232 |
| 5,759,003 A | 6/1998 | Greenway | |
| 5,899,938 A * | 5/1999 | Sklar et al. | 623/13.14 |
| 5,904,683 A | 5/1999 | Pohndorf | |
| 5,921,986 A * | 7/1999 | Bonutti | 606/60 |
| 5,931,840 A | 8/1999 | Goble | |
| 5,968,078 A | 10/1999 | Grotz | |
| 6,042,609 A * | 3/2000 | Giordano et al. | 424/423 |
| 6,056,752 A * | 5/2000 | Roger | 623/13.12 |
| 6,074,409 A | 6/2000 | Goldfarb | |
| 6,080,154 A * | 6/2000 | Reay-Young et al. | 606/60 |
| 6,099,530 A * | 8/2000 | Simonian et al. | 606/75 |
| 6,099,568 A * | 8/2000 | Simonian et al. | 623/13.11 |
| 6,102,934 A | 8/2000 | Li | |
| 6,110,207 A * | 8/2000 | Eichhorn et al. | 623/13.14 |
| 6,168,360 B1 | 1/2001 | Knox | |
| 6,190,411 B1 | 2/2001 | Lo | |
| 6,193,754 B1 * | 2/2001 | Seedhom | 623/13.11 |
| 6,214,007 B1 * | 4/2001 | Anderson | 606/304 |
| 6,221,107 B1 * | 4/2001 | Steiner et al. | 623/13.14 |
| 6,235,033 B1 | 5/2001 | Brace | |
| 6,241,731 B1 * | 6/2001 | Fiz | 606/65 |
| 6,254,605 B1 | 7/2001 | Howell | |
| 6,264,676 B1 | 7/2001 | Gellman | |
| 6,331,179 B1 * | 12/2001 | Freid et al. | 606/279 |
| 6,336,940 B1 * | 1/2002 | Graf et al. | 623/13.14 |
| 6,352,538 B2 | 3/2002 | McGuire | |
| 6,419,700 B2 | 7/2002 | Huene | |
| 6,464,706 B1 * | 10/2002 | Winters | 623/13.14 |
| 6,482,210 B1 * | 11/2002 | Skiba et al. | 606/86 R |
| 6,517,579 B1 * | 2/2003 | Paulos et al. | 623/13.14 |
| 6,533,802 B2 * | 3/2003 | Bojarski et al. | 606/232 |
| 6,547,800 B2 * | 4/2003 | Foerster et al. | 606/151 |
| 6,562,044 B1 * | 5/2003 | Cooper | 606/300 |
| 6,562,071 B2 * | 5/2003 | Jarvinen | 623/13.14 |
| 6,579,295 B1 * | 6/2003 | Supinski | 623/13.14 |
| 6,602,255 B1 | 8/2003 | Campbell | |
| 6,626,910 B1 | 9/2003 | Hugues | |
| 6,833,005 B1 | 12/2004 | Mantas | |
| 6,902,573 B2 * | 6/2005 | Strobel et al. | 606/232 |
| 6,921,401 B2 * | 7/2005 | Lerch et al. | 606/324 |
| 6,994,725 B1 | 2/2006 | Goble | |
| 7,032,599 B2 | 4/2006 | May | |
| 7,083,647 B1 * | 8/2006 | Sklar et al. | 623/13.14 |
| 7,097,654 B1 | 8/2006 | Freedland | |
| 7,172,595 B1 * | 2/2007 | Goble | 606/86 A |
| 7,211,111 B2 | 5/2007 | Boucher | |
| 7,261,716 B2 * | 8/2007 | Strobel et al. | 606/314 |
| 7,309,355 B2 * | 12/2007 | Donnelly et al. | 623/13.14 |
| 7,329,281 B2 * | 2/2008 | Hays et al. | 623/13.14 |
| 7,357,803 B2 | 4/2008 | Singhatat | |
| 7,455,683 B2 * | 11/2008 | Geissler et al. | 606/232 |
| 7,491,217 B1 * | 2/2009 | Hendren et al. | 606/232 |
| 7,530,990 B2 * | 5/2009 | Perriello et al. | 606/232 |
| 7,651,495 B2 | 1/2010 | McDevitt | |
| 7,678,138 B2 | 3/2010 | Fitts | |
| 7,708,738 B2 | 5/2010 | Fourcault | |
| 7,713,285 B1 * | 5/2010 | Stone et al. | 606/232 |
| 7,736,380 B2 | 6/2010 | Johnston | |
| 7,776,039 B2 | 8/2010 | Bernstein | |
| 7,875,057 B2 * | 1/2011 | Cook et al. | 606/232 |
| 7,896,901 B2 | 3/2011 | Whittaker | |
| 7,963,984 B2 | 6/2011 | Goble | |
| 7,967,861 B2 * | 6/2011 | Montgomery et al. | 623/13.15 |
| 7,972,341 B2 | 7/2011 | Berberich | |
| 8,080,013 B2 | 12/2011 | Whittaker | |
| 8,226,714 B2 * | 7/2012 | Beck et al. | 623/13.12 |
| 8,231,674 B2 * | 7/2012 | Albertorio et al. | 623/13.14 |
| 8,282,675 B2 | 10/2012 | Maguire | |
| 8,317,825 B2 * | 11/2012 | Stone | 606/213 |
| 8,323,338 B2 * | 12/2012 | LeBeau et al. | 623/13.14 |
| 8,388,655 B2 * | 3/2013 | Fallin et al. | 606/232 |
| 8,454,654 B2 * | 6/2013 | Ferragamo et al. | 606/232 |
| 8,460,379 B2 * | 6/2013 | Albertorio et al. | 623/13.14 |
| 8,470,037 B2 * | 6/2013 | Re et al. | 623/13.14 |
| D685,958 S * | 7/2013 | Wolfson | D30/154 |
| 8,486,116 B2 | 7/2013 | Heilman | |
| 8,500,784 B2 | 8/2013 | Hulliger | |
| 8,591,578 B2 * | 11/2013 | Albertorio et al. | 623/13.13 |
| 8,628,573 B2 * | 1/2014 | Roller et al. | 623/13.14 |
| 8,864,797 B2 * | 10/2014 | Justin et al. | 606/232 |
| 8,876,900 B2 * | 11/2014 | Guederian et al. | 623/13.14 |
| 8,888,815 B2 * | 11/2014 | Holmes, Jr. | 606/232 |
| 8,926,661 B2 * | 1/2015 | Sikora et al. | 606/232 |
| 8,968,364 B2 * | 3/2015 | Berelsman et al. | 606/232 |
| 2002/0013623 A1 * | 1/2002 | Sklar | 623/13.17 |
| 2002/0055780 A1 * | 5/2002 | Sklar | 623/13.12 |
| 2002/0072797 A1 * | 6/2002 | Hays et al. | 623/13.14 |
| 2002/0116013 A1 * | 8/2002 | Gleason et al. | 606/151 |
| 2002/0120274 A1 * | 8/2002 | Overaker et al. | 606/72 |
| 2002/0151899 A1 | 10/2002 | Bailey | |
| 2002/0161401 A1 * | 10/2002 | Steiner | 606/232 |
| 2002/0161439 A1 * | 10/2002 | Strobel et al. | 623/13.14 |
| 2002/0165547 A1 * | 11/2002 | Dovesi et al. | 606/73 |
| 2002/0188305 A1 * | 12/2002 | Foerster et al. | 606/151 |
| 2003/0023304 A1 * | 1/2003 | Carter et al. | 623/13.14 |
| 2003/0032982 A1 * | 2/2003 | Bonutti et al. | 606/232 |
| 2003/0040795 A1 * | 2/2003 | Elson et al. | 623/13.12 |
| 2003/0065390 A1 * | 4/2003 | Justin et al. | 623/13.14 |
| 2003/0105462 A1 | 6/2003 | Haider | |
| 2003/0130695 A1 * | 7/2003 | McDevitt et al. | 606/232 |
| 2003/0130735 A1 | 7/2003 | Rogalski | |
| 2004/0024456 A1 * | 2/2004 | Brown et al. | 623/13.15 |
| 2004/0073306 A1 * | 4/2004 | Eichhorn et al. | 623/13.11 |
| 2004/0153153 A1 * | 8/2004 | Elson et al. | 623/13.14 |
| 2004/0158244 A1 | 8/2004 | Clark | |
| 2004/0230196 A1 * | 11/2004 | Martello | 606/73 |
| 2004/0267361 A1 * | 12/2004 | Donnelly et al. | 623/13.14 |
| 2005/0033366 A1 | 2/2005 | Cole | |
| 2005/0065533 A1 * | 3/2005 | Magen et al. | 606/102 |
| 2005/0090827 A1 * | 4/2005 | Gedebou | 606/72 |
| 2005/0107828 A1 * | 5/2005 | Reese | 606/232 |
| 2005/0149121 A1 * | 7/2005 | Crombie et al. | 606/232 |
| 2005/0159812 A1 * | 7/2005 | Dinger et al. | 623/13.14 |
| 2005/0192632 A1 * | 9/2005 | Geissler et al. | 606/232 |
| 2005/0251137 A1 | 11/2005 | Ball | |
| 2005/0261766 A1 | 11/2005 | Chervitz | |
| 2006/0052787 A1 * | 3/2006 | Re et al. | 606/72 |
| 2006/0064126 A1 * | 3/2006 | Fallin et al. | 606/232 |
| 2006/0089711 A1 * | 4/2006 | Dolan | 623/2.37 |

(56) References Cited

U.S. PATENT DOCUMENTS

| | | | |
|---|---|---|---|
| 2006/0100626 A1 | 5/2006 | Rathbun | |
| 2006/0122604 A1 | 6/2006 | Gorhan | |
| 2006/0122608 A1* | 6/2006 | Fallin et al. | 606/72 |
| 2006/0149258 A1 | 7/2006 | Sousa | |
| 2006/0189993 A1* | 8/2006 | Stone | 606/73 |
| 2006/0271060 A1 | 11/2006 | Gordon | |
| 2006/0293669 A1 | 12/2006 | Lindemann | |
| 2007/0038221 A1 | 2/2007 | Fine | |
| 2007/0055255 A1* | 3/2007 | Siegel | 606/72 |
| 2007/0073342 A1* | 3/2007 | Stone et al. | 606/232 |
| 2007/0123988 A1 | 5/2007 | Coughlin | |
| 2007/0179531 A1 | 8/2007 | Thornes | |
| 2007/0193419 A1 | 8/2007 | Melton | |
| 2007/0233110 A1 | 10/2007 | Muhanna | |
| 2007/0233128 A1 | 10/2007 | Schmieding | |
| 2007/0233151 A1 | 10/2007 | Chudik | |
| 2007/0270857 A1* | 11/2007 | Lombardo et al. | 606/72 |
| 2008/0009904 A1* | 1/2008 | Bourque et al. | 606/232 |
| 2008/0033441 A1 | 2/2008 | Shino | |
| 2008/0046009 A1 | 2/2008 | Albertorio | |
| 2008/0046091 A1 | 2/2008 | Weiss | |
| 2008/0097604 A1* | 4/2008 | Strobel et al. | 623/13.14 |
| 2008/0103506 A1 | 5/2008 | Volpi | |
| 2008/0109037 A1* | 5/2008 | Steiner et al. | 606/232 |
| 2008/0154314 A1* | 6/2008 | McDevitt | 606/304 |
| 2008/0161852 A1* | 7/2008 | Kaiser et al. | 606/232 |
| 2008/0177302 A1* | 7/2008 | Shurnas | 606/228 |
| 2008/0177386 A1* | 7/2008 | Cerundolo | 623/13.14 |
| 2008/0183220 A1 | 7/2008 | Glazer | |
| 2008/0183290 A1* | 7/2008 | Baird et al. | 623/13.14 |
| 2008/0208204 A1 | 8/2008 | Schmieding | |
| 2008/0228271 A1* | 9/2008 | Stone et al. | 623/13.12 |
| 2008/0269743 A1* | 10/2008 | McNamara et al. | 606/60 |
| 2008/0275553 A1* | 11/2008 | Wolf et al. | 623/13.14 |
| 2008/0288070 A1* | 11/2008 | Lo | 623/13.14 |
| 2008/0306510 A1* | 12/2008 | Stchur | 606/232 |
| 2008/0306511 A1* | 12/2008 | Cooper et al. | 606/232 |
| 2009/0018654 A1 | 1/2009 | Schmieding | |
| 2009/0030516 A1 | 1/2009 | Imbert | |
| 2009/0149884 A1* | 6/2009 | Snyder et al. | 606/233 |
| 2009/0216282 A1 | 8/2009 | Blake | |
| 2009/0228013 A1 | 9/2009 | Bourque | |
| 2009/0270927 A1 | 10/2009 | Perrow | |
| 2009/0292301 A1 | 11/2009 | Hasselman | |
| 2009/0292321 A1* | 11/2009 | Collette | 606/303 |
| 2009/0306777 A1 | 12/2009 | Widmer | |
| 2009/0312794 A1* | 12/2009 | Nason et al. | 606/232 |
| 2010/0047309 A1* | 2/2010 | Lu et al. | 424/423 |
| 2010/0063541 A1* | 3/2010 | Brunelle et al. | 606/232 |
| 2010/0069958 A1* | 3/2010 | Sullivan et al. | 606/232 |
| 2010/0100182 A1* | 4/2010 | Barnes et al. | 623/13.14 |
| 2010/0125297 A1* | 5/2010 | Guederian et al. | 606/232 |
| 2010/0174369 A1* | 7/2010 | Wang et al. | 623/13.14 |
| 2010/0249930 A1 | 9/2010 | Myers | |
| 2010/0262184 A1* | 10/2010 | Dreyfuss | 606/228 |
| 2010/0262185 A1* | 10/2010 | Gelfand et al. | 606/232 |
| 2010/0268273 A1 | 10/2010 | Albertorio | |
| 2010/0274356 A1* | 10/2010 | Fening et al. | 623/13.14 |
| 2010/0318188 A1* | 12/2010 | Linares | 623/13.14 |
| 2010/0324676 A1* | 12/2010 | Albertorio et al. | 623/13.14 |
| 2010/0331899 A1 | 12/2010 | Garcia | |
| 2011/0034933 A1 | 2/2011 | Paulos | |
| 2011/0053109 A1 | 3/2011 | Zipprich | |
| 2011/0071579 A1* | 3/2011 | Reach, Jr. | 606/327 |
| 2011/0087280 A1 | 4/2011 | Albertorio | |
| 2011/0106171 A1 | 5/2011 | Kirschman | |
| 2011/0118838 A1* | 5/2011 | Delli-Santi et al. | 623/13.14 |
| 2011/0160856 A1* | 6/2011 | Sinnott et al. | 623/13.14 |
| 2011/0190886 A1* | 8/2011 | Li | 623/13.19 |
| 2011/0196490 A1* | 8/2011 | Gadikota et al. | 623/13.14 |
| 2011/0208194 A1 | 8/2011 | Steiner | |
| 2011/0218625 A1* | 9/2011 | Berelsman et al. | 623/13.14 |
| 2011/0270326 A1* | 11/2011 | Black et al. | 606/308 |
| 2011/0282350 A1 | 11/2011 | Kowarsch | |
| 2011/0301708 A1* | 12/2011 | Stone et al. | 623/13.14 |
| 2012/0022593 A1 | 1/2012 | Kovach | |
| 2012/0029577 A1 | 2/2012 | Kerr | |
| 2012/0059469 A1* | 3/2012 | Myers et al. | 623/13.14 |
| 2012/0078369 A1* | 3/2012 | Hart | 623/13.14 |
| 2012/0083837 A1 | 4/2012 | Ferragamo | |
| 2012/0109299 A1* | 5/2012 | Li et al. | 623/13.14 |
| 2012/0123541 A1* | 5/2012 | Albertorio | 623/13.14 |
| 2012/0130492 A1* | 5/2012 | Eggli et al. | 623/13.14 |
| 2012/0150203 A1* | 6/2012 | Brady et al. | 606/148 |
| 2012/0165938 A1* | 6/2012 | Denham et al. | 623/13.14 |
| 2012/0203340 A1* | 8/2012 | Choinski et al. | 623/13.14 |
| 2012/0245632 A1* | 9/2012 | Tsai et al. | 606/232 |
| 2012/0303071 A1 | 11/2012 | Black | |
| 2013/0110163 A1* | 5/2013 | Ballard et al. | 606/232 |
| 2013/0110164 A1* | 5/2013 | Milazzo et al. | 606/232 |
| 2013/0116787 A1* | 5/2013 | Ferragamo et al. | 623/13.14 |
| 2013/0123841 A1* | 5/2013 | Lyon | 606/232 |
| 2013/0204366 A1* | 8/2013 | Spenciner et al. | 623/13.14 |
| 2013/0204367 A1* | 8/2013 | Perriello et al. | 623/13.14 |
| 2013/0297020 A1* | 11/2013 | Wolfson et al. | 623/13.13 |
| 2014/0074160 A1* | 3/2014 | Denham et al. | 606/232 |
| 2014/0081323 A1* | 3/2014 | Hawkins | 606/232 |
| 2014/0094912 A1* | 4/2014 | Walker | 623/13.14 |
| 2014/0114352 A1* | 4/2014 | Allen | 606/232 |
| 2014/0155937 A1* | 6/2014 | Shinde | 606/232 |
| 2014/0172095 A1* | 6/2014 | Graf et al. | 623/13.14 |
| 2014/0277447 A1* | 9/2014 | Berelsman et al. | 623/13.14 |
| 2014/0303729 A1* | 10/2014 | Lee | 623/13.12 |
| 2014/0309691 A1* | 10/2014 | Brown et al. | 606/232 |
| 2014/0358230 A1* | 12/2014 | Niese et al. | 623/13.14 |
| 2015/0018878 A1* | 1/2015 | Rizk et al. | 606/232 |
| 2015/0025631 A1* | 1/2015 | Bouduban et al. | 623/13.14 |
| 2015/0032154 A1* | 1/2015 | Kaplan | 606/228 |

FOREIGN PATENT DOCUMENTS

| | | |
|---|---|---|
| EP | 1716874 | 11/2006 |
| EP | 1813226 | 8/2007 |
| EP | 2462876 | 6/2012 |
| FR | 2926456 | 7/2009 |
| GB | 2225547 | 6/1990 |
| GB | 2288739 | 11/1995 |
| WO | WO9400058 | 1/1994 |
| WO | WO9811838 A1 | 3/1998 |
| WO | WO2004043278 | 5/2004 |
| WO | WO2007073563 | 11/2007 |
| WO | WO2008129241 | 10/2008 |
| WO | WO2012154922 | 11/2012 |

* cited by examiner

GRAFT FIXATION

CROSS-REFERENCE TO RELATED APPLICATIONS

This application claims the benefit of prior U.S. Provisional Patent Application No. 61/770,000 filed Feb. 27, 2013, and is entitled GRAFT FIXATION. The above-identified documents are incorporated herein by reference.

BACKGROUND

1. Technical Field

The present disclosure relates to graft fixation including Anterior Cruciate Ligament (ACL) graft reconstruction and fixation. More specifically this disclosure relates to (1) ACL graft strand fixation within a bone tunnel and (2) extra-cortical fixation of a graft with an extra-cortical fixation loop fixation device, or button. The present disclosure also relates to methods for using the devices. It is also contemplated that the systems and methods provided herein, or any adaptations, may be useful outside of and beyond ACL graft construction and fixation and beyond any sports medicine knee repair.

2. The Relevant Technology

One attribute of ACL repair surgery is the fixation of the ACL graft through a bone tunnel providing intra-cortical and extra-cortical fixation. Adequate fixation to maintain the graft and appropriate tension is the common challenge. Therefore, there is a need to have adequate graft fixation either through intra-cortical or extra-cortical fixation as necessary for the specific patient's needs while maintaining a minimal extra-cortical profile regardless of the type of fixation, either an extra-cortical fixation loop fixation device or a bone tunnel and sleeve construct.

The implants described herein are designed to be utilized with bone tunnels that are drilled or reamed from the outside surfaces of the bone towards the central notch where the ACL resides. This methodology provides access for implantation through individual incisions through the skin.

The implants described herein are designed to work within shortened all-epiphyseal tunnels in comparison to more traditional reconstruction methods. The loop fixation construct was designed specifically with the intent to maximize graft to tunnel contact area so as to promote healing. The screw and sleeve construct was developed as a means of obtaining comparable fixation strengths within shorter tunnel lengths.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION

The present invention relates to ACL graft reconstruction and fixation. The following description illustrates the principles of the invention, which may be applied in various ways to provide many different alternative embodiments. This description is not meant to limit the inventive concepts in the appended claims.

The present technology may be employed in an ACL graft retention device for ACL and other sports medicine and soft tissue repair. The present technology may provide firm graft retention from a cortical fixation device or a device for fixing a graft within a bone-tunnel. While exemplary embodiments of the present technology have been shown and described in detail below, it will be clear to the person skilled in the art that changes and modifications may be made without departing from its scope. As such, that which is set forth in the following description and accompanying drawings is offered by way of illustration only and not as a limitation. In addition, one of ordinary skill in the art will appreciate upon reading and understanding this disclosure that other variations for the technology described herein can be included within the scope of the present technology.

Referring to FIGS. 32A-32E, a system may be used for ACL graft reconstruction. The system may include a body 10, a sleeve 210 and a screw 300. A first tunnel 3102 is prepared in a tibial socket 3104, which may be referred to as first member. A second tunnel 3106 is prepared in a femoral socket 3108, which may be referred to as second member. The sleeve 210 is engaged with the second tunnel 3106 at a proximal end 3110. A loop 3312 is formed using a graft 3314, which may be referred to as a flexible member. The loop 3312 is inserted into the second tunnel 3106. The loop 3312 is passed through the second tunnel 3106 and the first tunnel 3102, and is made accessible outside the first tunnel 3102. At least a portion of the body 10 is placed underneath the loop 3312. Subsequently, the loop 3312 is pulled towards the proximal end 3110 of the second tunnel 3106 until further movement of the graft 3314 is restricted by a portion of the body 10, which engages with an outside surface 3316 of the tibial socket 3104. Thereafter, the screw 300 is engaged with the sleeve 210. The engagement of the screw 300 and the sleeve 210 results in securing of the graft 3314 at the proximal end 3110 of the second tunnel 3106 defined in the femoral socket 3108.

Figure 1:
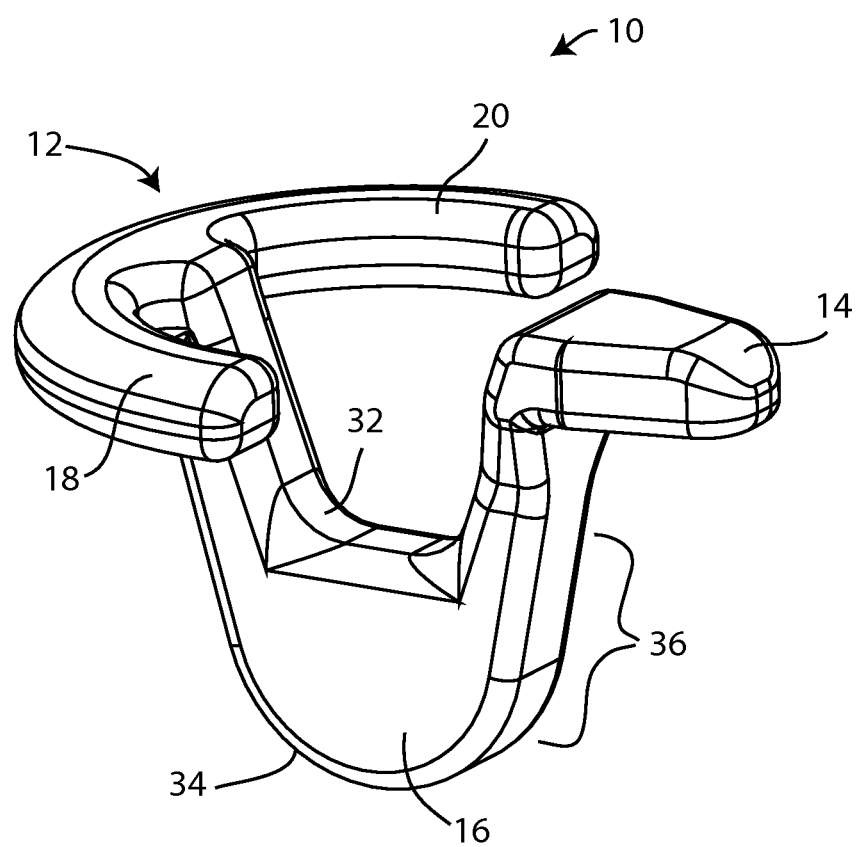
FIG. 1 is a perspective view of a loop fixation device, or button, or body.
Figure 2:
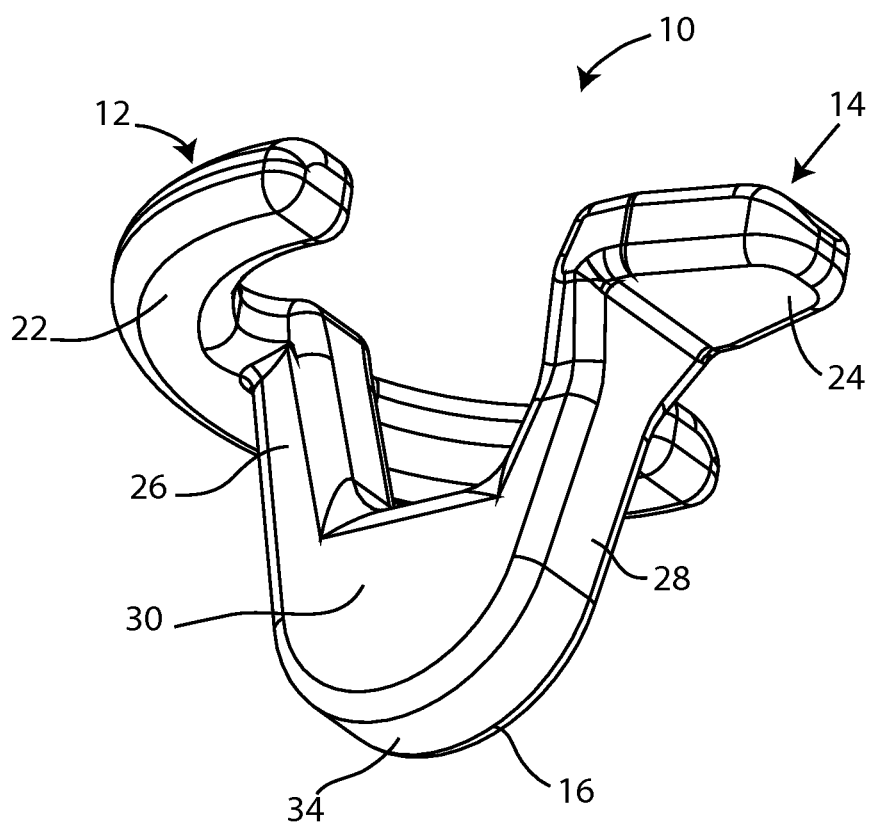
FIG. 2 is a bottom perspective view of the loop fixation device of FIG. 1.
Figure 3:
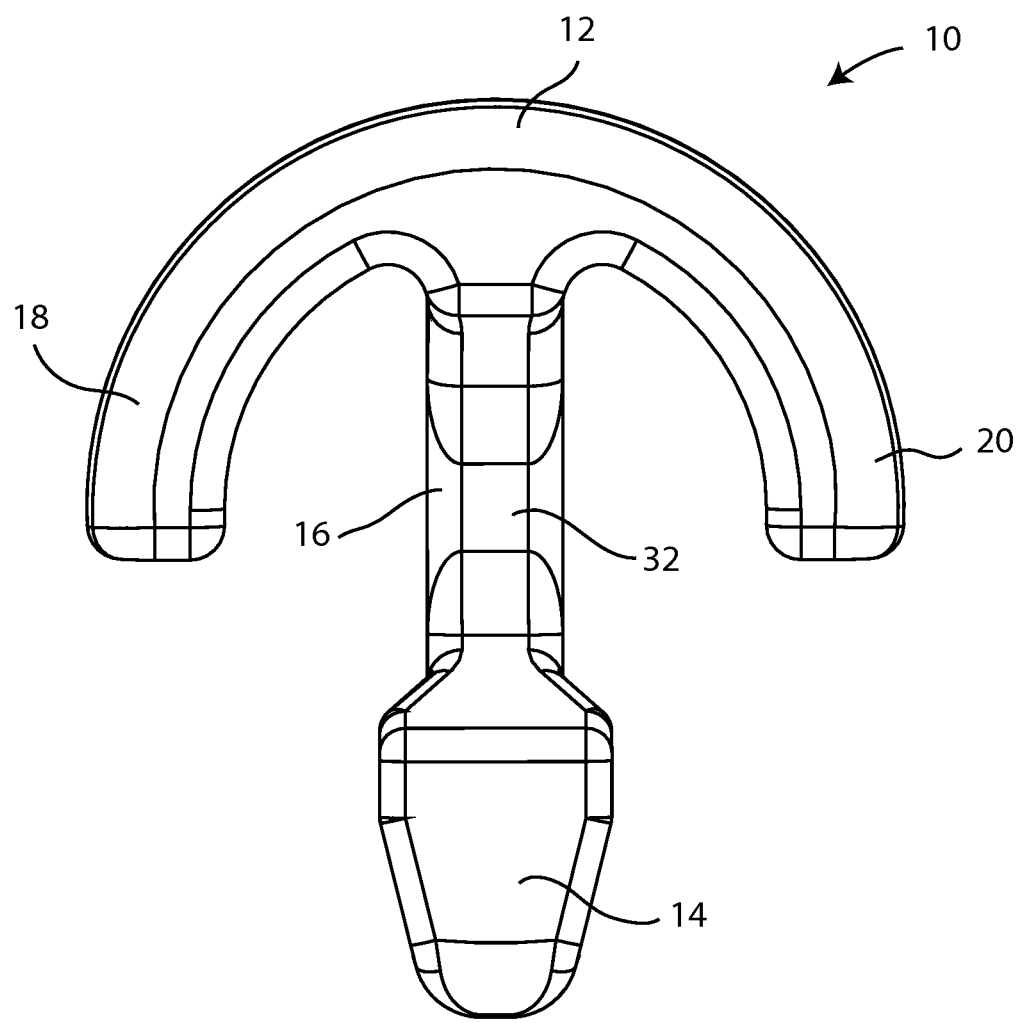
FIG. 3 is a top view of the loop fixation device of FIG. 1.

Referring to FIGS. 1-3, a body 10, which may be a cortical loop fixation device, or loop fixation button, or button, includes a single piece that may perform two functions. The body 10 may include a first flange 12. A second flange 14 may also be present, but separate from the first flange 12. One or more such flanges may be referred to as engagement means. The first flange 12 may be substantially circular on a top portion of the body 10. The second flange 14 may be considered a lip for a protrusion. Between the first and second flanges 12,14 is a retention portion 16. The retention portion 16 may also be referred to as graft retention portion or a graft hook, or retention means. The retention portion 16 connects the first and second flanges 12,14.

The first and second flanges 12, 14 may lie in a plane that is normal to the retention portion 16. A plane about which the retention portion 16 is at least substantially symmetrical may be perpendicular to a plane in which the first and second flanges 12,14 may lie.

The first flange 12 may include an engaging surface 22. Likewise, the second flange 14 may include an engaging surface 24. A plane in which the engaging surface 22 of the first flange 12 lies may be perpendicular to the plane about which the retention portion 16 is at least substantially symmetrical. Likewise, a plane in which the engaging surface 24 of the second flange 14 lies, may be perpendicular to a plane about which the retention portion 16 is at least substantially symmetrical.

In an embodiment, a plane in which the engaging surface of the first flange lies may be oblique to the plane about which the retention portion 16 is at least substantially symmetrical. Likewise, a plane in which the engaging surface of the second flange lies may be oblique to a plane about which the retention portion 16 is at least substantially symmetrical.

In another embodiment, a plane in which the engaging surface of the first flange lies may be oblique to the plane about which the retention portion 16 is at least substantially symmetrical. Whereas a plane in which the engaging surface of the second flange lies may be perpendicular to a plane about which the retention portion 16 is at least substantially symmetrical.

In yet another embodiment, a plane in which the engaging surface of the first flange lies, may be oblique to a plane about which the engaging surface of the second flange lies.

In an embodiment, at least one of the engaging surfaces of the flanges has a flat configuration.

In another embodiment, at least one of the engaging surfaces of the flanges has a curved configuration.

In yet another embodiment, at least one of the engaging surfaces of the flanges compliment the topography of a surface with which it interfaces.

The alignment of the first flange, the second flange and the retention portion with respect to each other is such that, engaging surfaces of each of the flanges adequately interface with corresponding cortical bone surfaces against which they may be pressed.

The flanges 12,14 are configured to rest on the cortical surface of a bone while the retention portion 16 is configured to rest inside a bone tunnel and engage a tissue graft. The retention portion 16 may be placed underneath the loop of a tissue graft outside of the bone tunnel. The retention portion 16 secures the tissue graft to the body 10, and the flanges 12,14 of the body 10 secure the body 10 to the bone.

As stated previously, the first flange 12 may be substantially circular wherein the arms 18,20 of the first flange 12 extend toward the second flange 14 in a circular projection and opposite each other where the first arm 18 may extend in a counter-clockwise direction and the second arm 20 may extend in a clockwise direction. The arms 18,20 may terminate forming a half circle and terminating prior to extending entirely to the second flange. However, it will be appreciated that the arms 18,20 may extend less than forming a half circle or greater than forming a half circle and may extend almost entirely to the second flange 14. A bone engaging surface 22 of the first flange 12 may be flat to engage the flat surface of the cortical bone.

The second flange 14 may include a large protrusion extending in a direction normal to the retention portion 16 and in a direction opposite the first flange 12. The second flange 14 may be a constant shape as it extends from the graft hook 16 or it may taper the further it extends. A bone engaging surface 24 of the second flange 14 may be flat, similar to that of the first flange 12, to engage the flat surface of the cortical bone. By engaging the cortical surface of the bone the flanges prevent the loop fixation device 10 from being drawn into the bone tunnel when the tissue graft is engaged and tensioned. The bone engaging surfaces 22, 24 may be textured, roughened, coated, or otherwise structured to positively engage bone in the short and/or long term.

The retention portion 16 may be V, U or J shaped to engage a tissue graft. A first leg 26 comprises one side of the U and a second leg 28 comprises the other side of the U with a retention portion or central portion 30, or graft interfacing portion, connecting the two legs 26,28. The central portion 30 may be rounded for a U or J shape or pointed for a V shape. The first leg 26 extends from the central portion 30 to the first flange 12, and the second leg 28 extends from the central portion 30 to the second flange 14. The central portion 30 may include a flat surface on the base of a first, inside, wall 32 or it may have a continuing rate of curvature with no flat surface.

The first and second legs may have the same length. Alternatively, the first and second legs may have the varying lengths.

The retention portion 16 includes a first, inside, wall 32 and a second, outside, wall 34. The transition from the central portion 30 to the legs, 26,28 may be abrupt forming hard angles on the inside wall 32 or it may be gradual with a continuing rate of curvature. However, it will be appreciated that the inside wall 32 may include hard angles in place of the smooth U or hook shaped transitions and may take a partial polygon shape as well. The outside wall 34 may match the curvature of the inside wall 32 and thus may form a substantially U-shape with a gradual smooth transition from one leg 26, 28 through the central portion 30 to the other leg 26,28. Although, fixed angles rather than a circular transition may also be considered for the outside wall 34 with a polygonal shape. The outside wall 34 is not required to match the curvature or shape of the inside wall 32.

The legs 26,28 of the graft hook 16 may extend non-parallel upward toward the flanges 12,14. In another embodiment the legs 26, 28 may extend parallel toward the flanges.

In an embodiment, surfaces of the legs 26,28 facing the graft may be parallel to each other, while surfaces of each of the legs 26,28, which are at least to some extent opposite to the surface of the legs 26,28 facing the graft, may be oblique to each other.

In an embodiment, one or more slots (or other resilient material or structure) may be defined in at least one of the legs 26, 28 and/or the central portion 30, such that, when force is applied on the legs 26,28 by wall of the tunnel when the body 10 is pulled into the tunnel, the legs 26, 28 are moved closer to each other, thereby defining an interference fit between the wall of the tunnel and the legs 26,28.

The central portion 30 of the retention portion 16 may have a larger side view footprint for engaging the tissue graft. The central portion 30 may comprise more material relative to the arms of the graft hook 16.

Referring to FIG. 3 it is shown that a top view of the loop fixation device may resemble an anchor.

Figure 4:
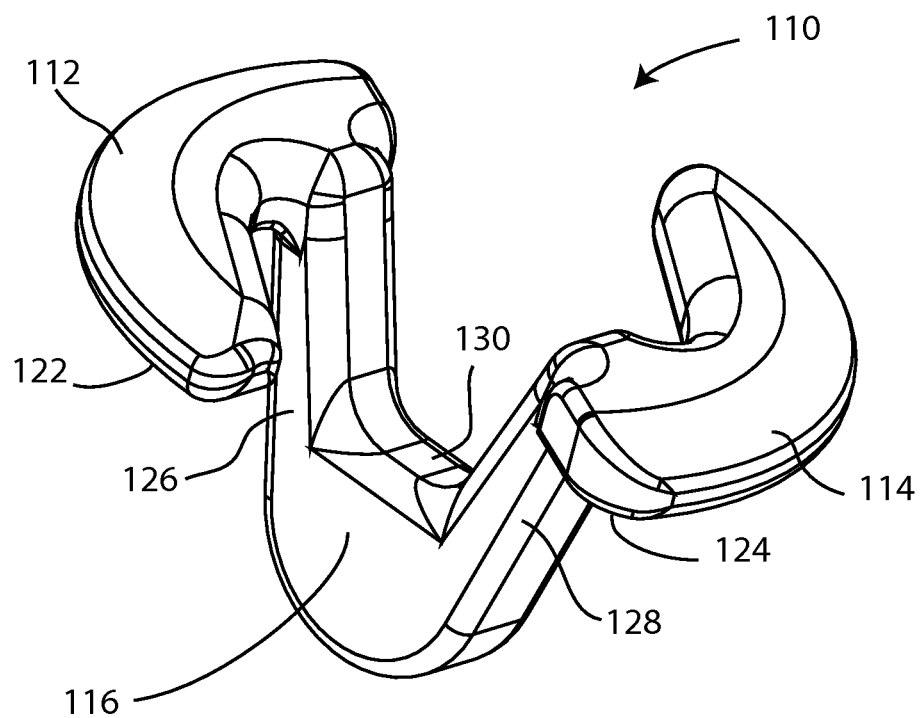
FIG. 4 is a perspective view of an alternate embodiment loop fixation device, or body.
Figure 5:
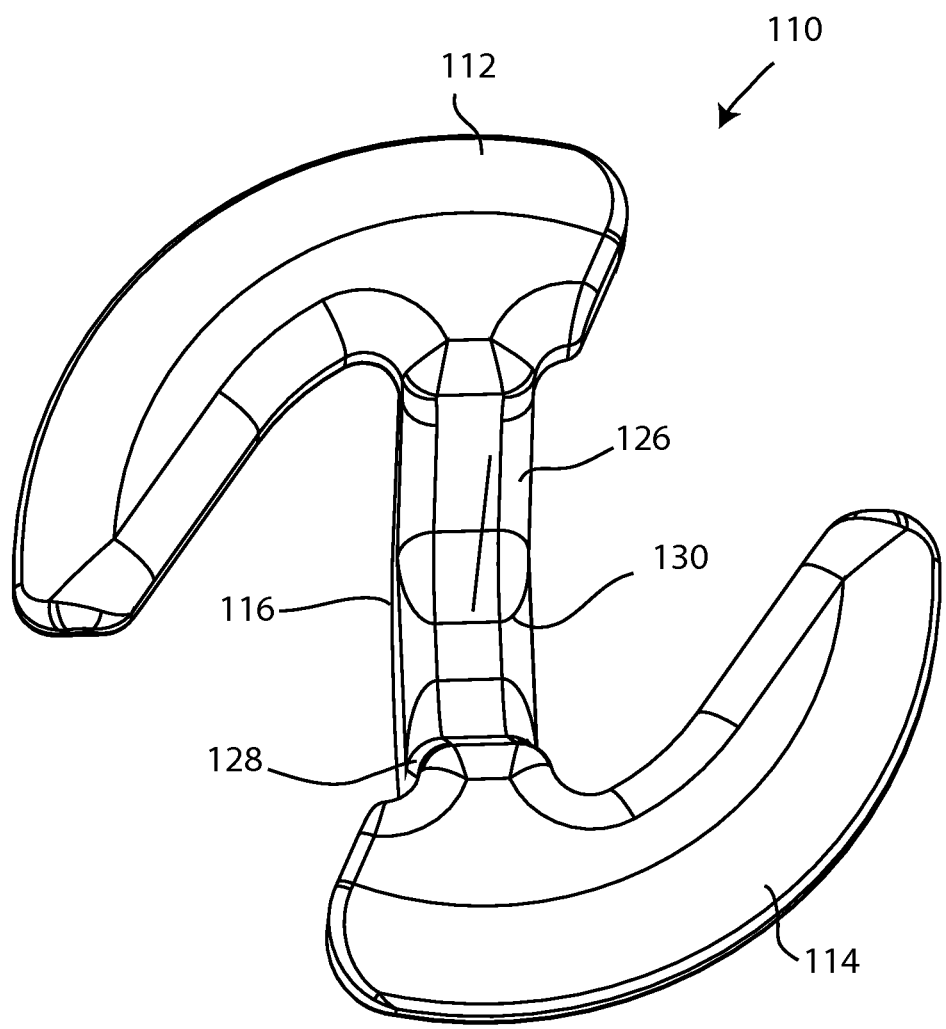
FIG. 5 is a top view of the loop fixation device of FIG. 4.

Referring to FIGS. 4 and 5, an alternate embodiment of a body, which may be a cortical loop fixation device 110 or system, includes a first flange 112 and a second flange 114, or first and second flange hooks because of their curved feature. The first and second flanges 112, 114 may extend in a circular fashion toward an opposite end of the loop fixation device 110 and in either a clockwise or counter-clockwise direction. The flanges 112,114 in this embodiment are extending in a counter clockwise direction and not intersecting; however, it will be appreciated that the flanges 112,114 may extend greater than or less than a quarter turn.

The loop fixation device 110 also includes a graft retention portion 116, or graft hook, which may be substantially similar to the previous embodiment with a central portion 130, or graft interfacing portion, or saddle, a first leg 126 and a second leg 128. The saddle 130 engages and maintains the graft. Similar to the previous embodiment, the flanges 112, 114 may include bone engaging surfaces 122, 124 on each of bottom surfaces of the flanges to engage the cortex of the bone. By engaging the cortex, the flanges 112,114 prevent the loop fixation device 110 from being drawn into the bone tunnel when the graft is engaged and tensioned.

Advantages to either embodiment of the loop fixation devices, 10, 110 is that neither loop fixation device may require toggling of the loop fixation device to appropriately position the loop fixation device. Another distinct advantage of these loop fixation devices 10,110 is no need for a flexible medium such as a suture or cord between the graft and the loop fixation device 10,110. Therefore, this technology contributes to increased stiffness of the entire graft reconstruction. Furthermore the loop fixation device 10,110 is positioned and engages the tissue graft outside of the bone tunnel and does not need to be passed through the bone tunnel. The loop fixation device 10,110 has less likelihood of falling inside the bone tunnel because of its shape and dimensions and is especially useful in instances and applications where surgeons ream the bone tunnel from the outside cortical bone toward the inside, intercondylar notch where the cortical wall around the proximal portion of the tunnel (the outside cortical portion) of the tunnel is no longer intact.

Figure 27A:
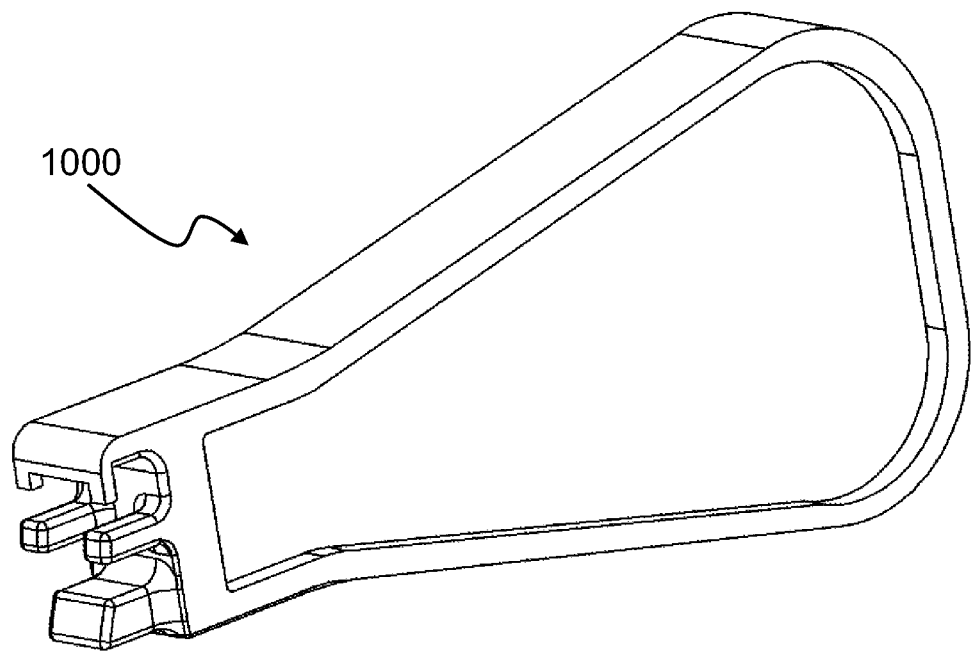
FIG. 27A is a perspective view of an installation instrument for use with the loop fixation device of FIG. 1.
Figure 27B:
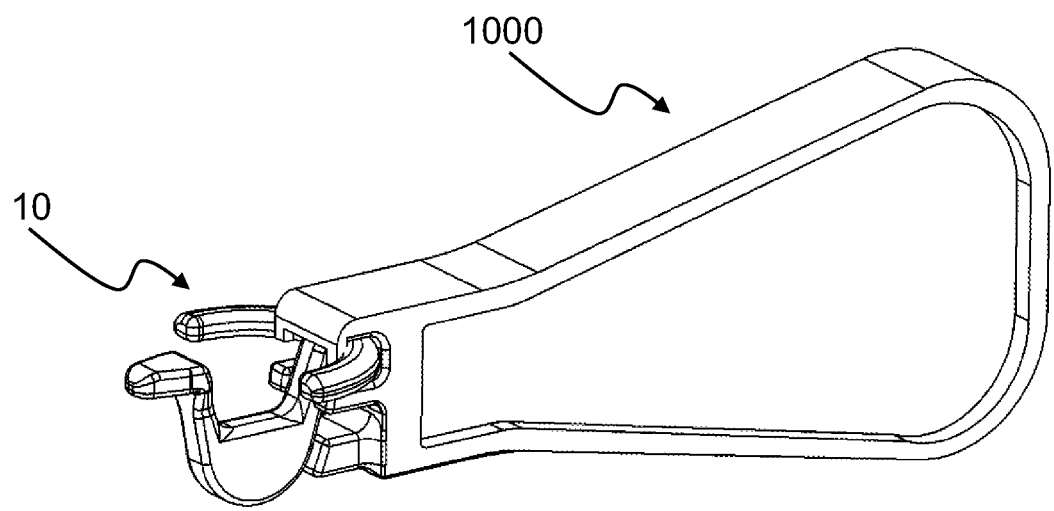
FIG. 27B is a perspective view of the installation instrument of FIG. 27A engaging the loop fixation device of FIG. 1.

Referring to FIGS. 27A and 27B, an installation instrument 1000 may be used to aid in the installation of the body 10 in connection with the graft 3314.

Figure 6:
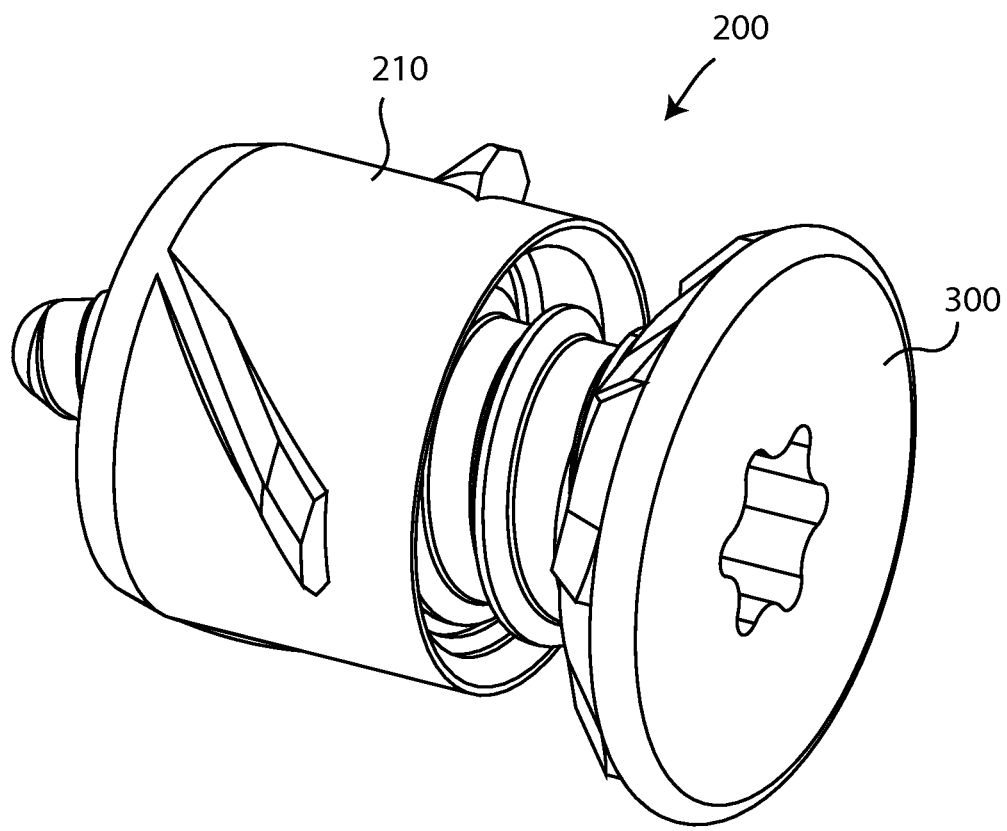
FIG. 6 is a semi-exploded perspective view of a sleeve and a screw.
Figure 7:
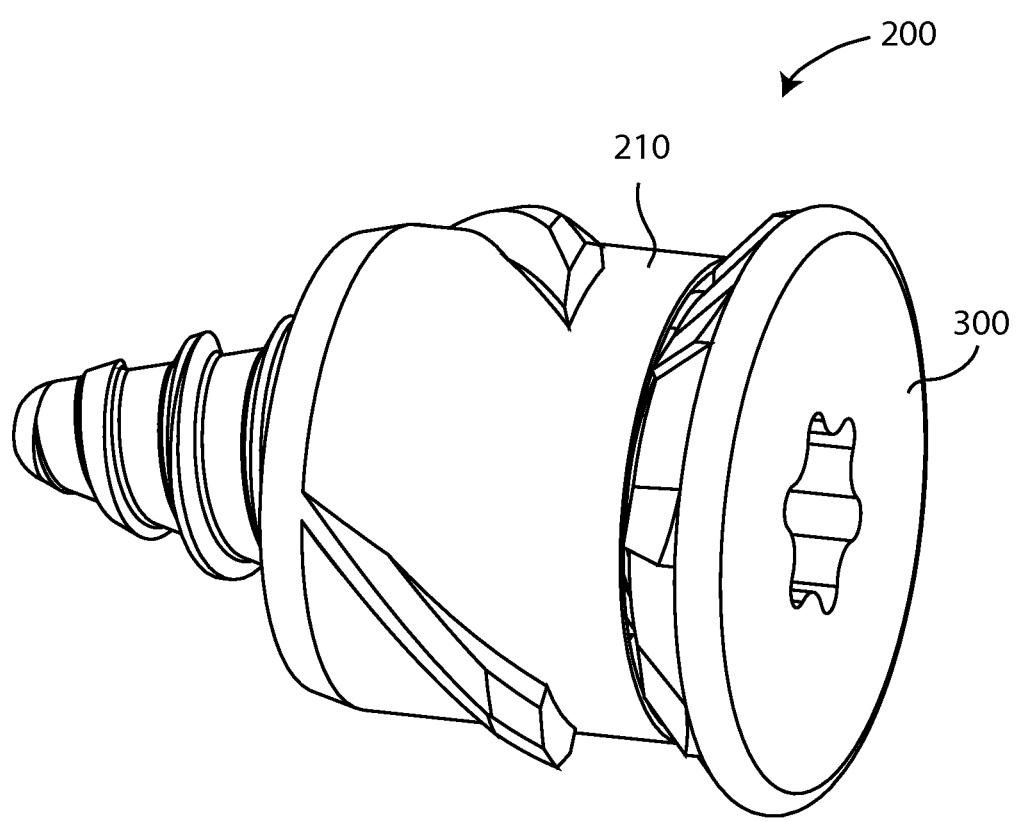
FIG. 7 is an engagement perspective view of the sleeve and the screw of FIG. 6.

A separate structure may be utilized to provide alternate graft fixation through the use of a sleeve and screw and will be described further herein. Referring to FIGS. 6, 7, 7A and 7B, a graft retention device 200 may include a sleeve 210 and a screw 300. The screw 300 may be inserted into the sleeve 210 after at least a portion of a tissue graft has passed through the sleeve 210. The screw 300 provides interference fixation of the tissue graft by radial force onto the tissue graft toward an inner wall of the sleeve 210 with the screw 300 as the screw is advanced further into the sleeve 210. FIG. 6 illustrates the screw 300 partially engaged within the sleeve 210 while FIG. 7 illustrates the screw 300 fully engaged within the sleeve 210.

Referring to FIGS. 6-10, the sleeve 210, which may be referred to as accommodation means, may be a cylinder, or tubular, with an inside wall 212 and an outside wall 214 with a bore 216, or tunnel, which may be a central bore and may be defined by a central axis, passing at least partially through the center thereof and may pass entirely, and longitudinally, through the sleeve 210. The inside wall 212 may include female threads for engaging a screw. It should be understood that the threads on the inside wall 212 may be replaced with ridges, a tooth or teeth or barbs or any other tractive features or means to allow the sleeve 210 to grab and capture the graft. The bore 216 may maintain a constant diameter through the entire sleeve 210 or the diameter may become smaller toward a distal end. The outside wall 214 may include radial fins 218 projecting from the outside wall 214. The fins 218 may provide anti-rotation of the sleeve 210 during installation of the screw 300 within the sleeve 210. In this situation, the fins 218 may twist counter-clockwise to resist screw insertion torque. The fins 218 may include a helical turn and have a larger cross-sectional footprint toward the proximal end of the sleeve 210. As the fins 218 advance toward the distal end, the fins 218 may taper to a point and eventually become flush with the outside wall 214 of the sleeve 210. The proximal end of the fins 218 may not reach the proximal end of the sleeve 218. The fins 218 may have a flat proximal surface 220 that is normal to the outside wall 214 of the sleeve and which may prevent withdrawal of the sleeve from out of a bone tunnel by providing an anti-back out feature.

The outside wall 214 may have a constant circumference from the proximal end to the distal end. Although, referring to FIG. 9, a taper 222 may extend from the distal end of the sleeve 210 wherein the circumference is relatively smaller than the main body of the sleeve 210. The fins 218 may extend into the taper 222 and become flush with the taper 222, the fins terminating at the taper 222. The taper 222 may provide a lead-in to aid in the introduction of the sleeve into the bone tunnel.

The sleeve 210 may contain the hoop stress of the screw impinging onto the graft. This may prove advantageous where the forces may become disruptive of nearby growth plates of growing children. The sleeve 210 provides more consistent clamping of the graft by providing stability and keeping the screw 300 from tracking off axis and outside the bounds of the bone tunnel while also providing a controlled exterior interface with the bone tunnel.

There may be a clearance between the inner wall 212 of the sleeve 210 and the screw 300 to allow for the tissue graft to pass through the sleeve and still allow the screw 300 to engage or be coupled to the sleeve 210. Referring to FIGS. 11-13B, the screw 300 includes a body 310 and a head 312. The body 310 may include threads 314, which may be male threads configured to engage the female threads of the inner wall 212 of the sleeve 210. The threads 314 of the screw 300 and the threads of the sleeve 210 may provide further traction to prevent slippage of the tissue graft along the tunnel sleeve axis. The body 310 may taper extending away from the head 312 toward a distal end allowing for easier insertion into the sleeve 210 when the tissue graft is within the sleeve 210.

A portion of the body 310 which engages the sleeve 210 may have a uniform cross-sectional diameter, whereas a portion of the body 310, which extends beyond the distal end of the sleeve 210 may taper towards the distal end of the screw 300.

The head 312 may include a flat proximal surface 316 with a central void 318, the central void 318 extending at least partially inward from the flat proximal surface toward a distal end to allow access for a surgical tool. The central void 318 may be star shaped, polygonal or any other shape to allow access of and engaging of a tool for insertion of the screw 300 into the sleeve 210 and the central void 318 may be entirely enclosed. The head 312 may have a larger diameter than the body 310 of the screw 300 wherein the diameter decreases from the head to the body creating a shoulder or lip such that the head 312 may rest against the cortex of the bone on the edge of the bone tunnel which may provide resistance to axial translation of the device 200. The head 312 may also include barbs 320, a tooth or teeth, positioned where the diameter is decreasing from the head 312 to the body which may also be the point where the tissue graft and the bone interface. The barbs 320 are configured in a direction to prevent the screw 300 from backing out.

Figure 7A:
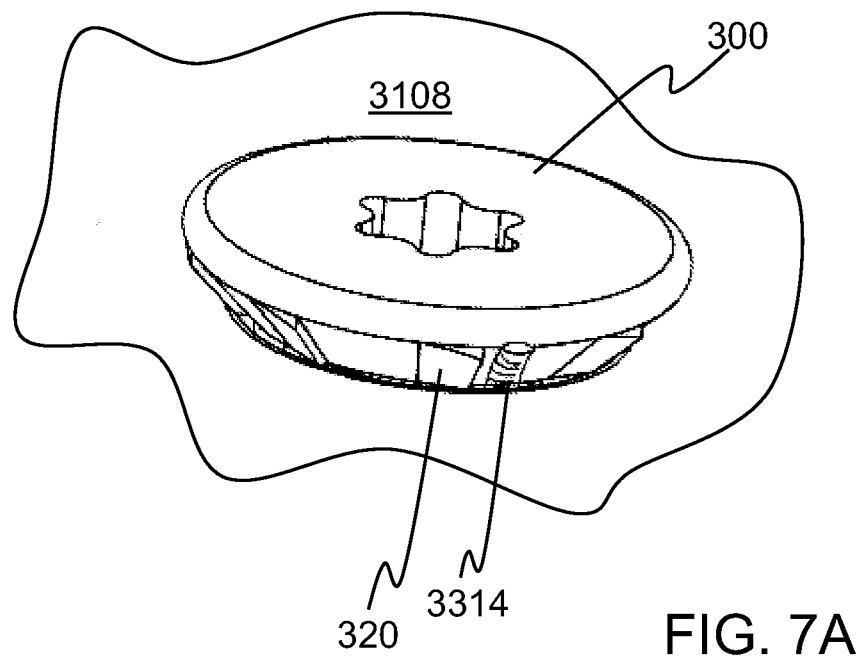
FIG. 7A is a perspective view of a graft interfacing the screw of FIG. 6.
Figure 7B:
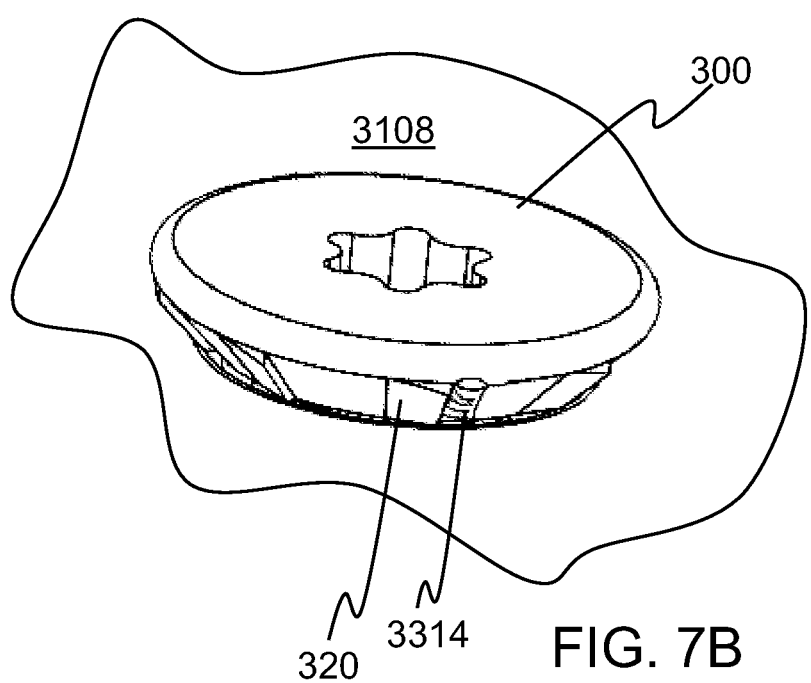
FIG. 7B is a perspective view of the graft restricting the screw from backing out.
Figure 8:
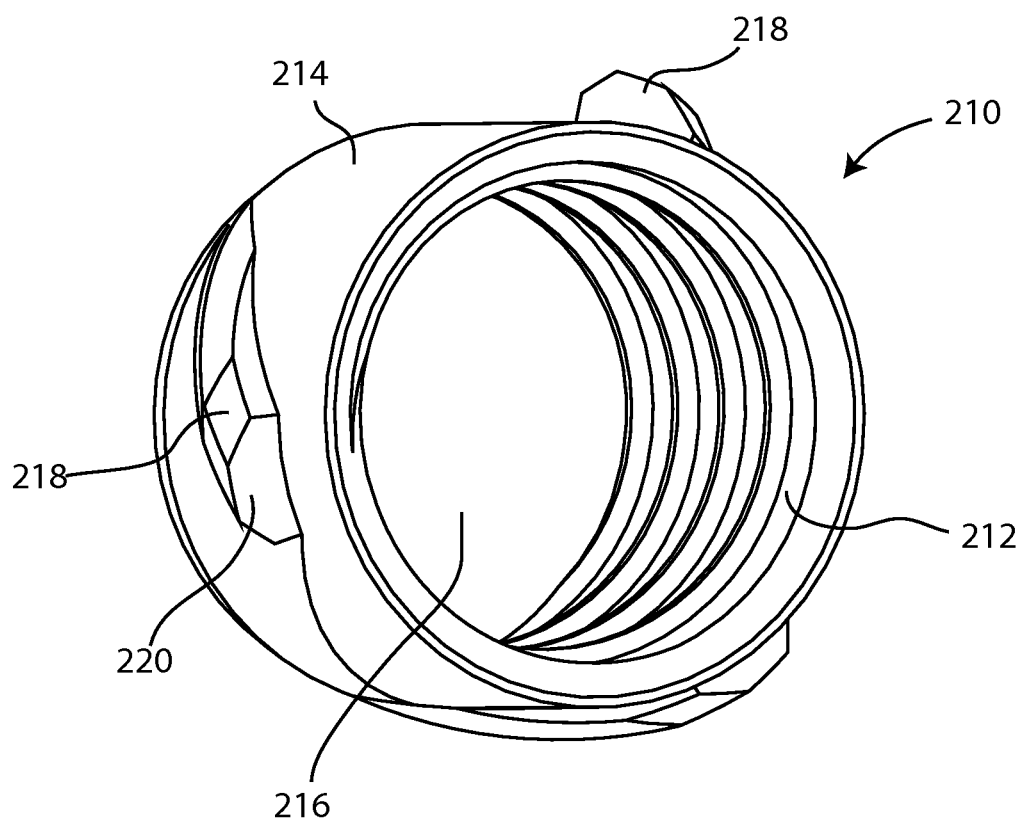
FIG. 8 is a perspective view of the sleeve of FIG. 6.
Figure 9:
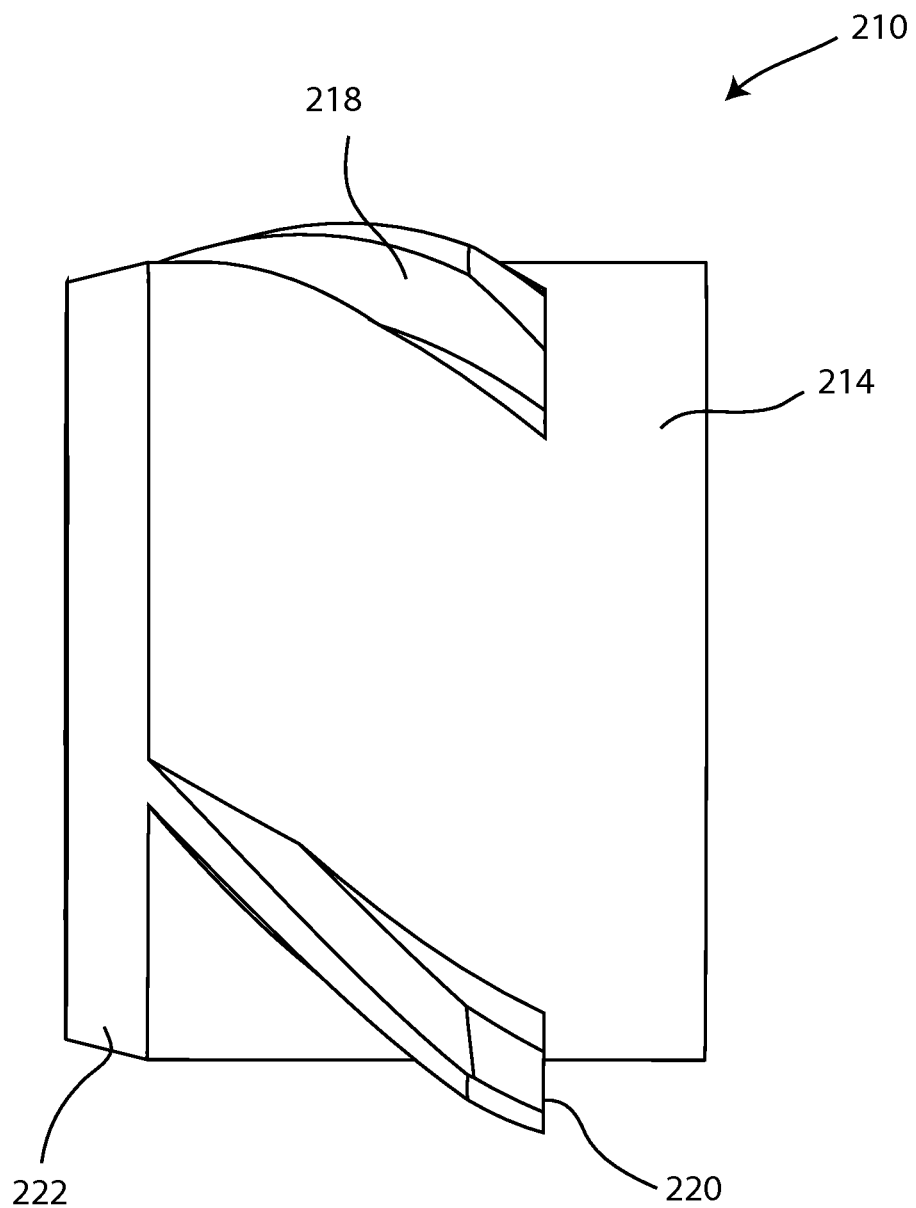
FIG. 9 is a side view of the sleeve of FIG. 6.
Figure 10:
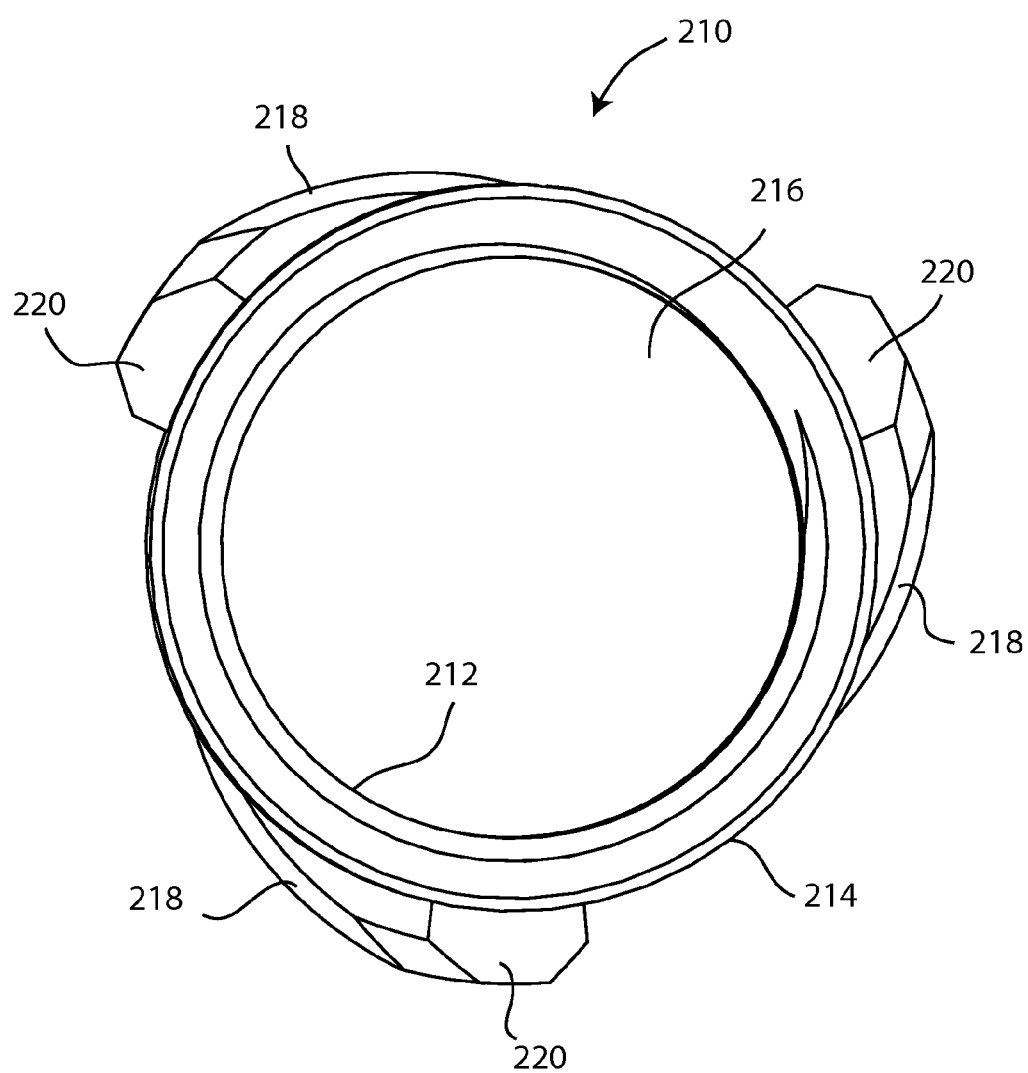
FIG. 10 is a top view of the sleeve of FIG. 6.
Figure 11:
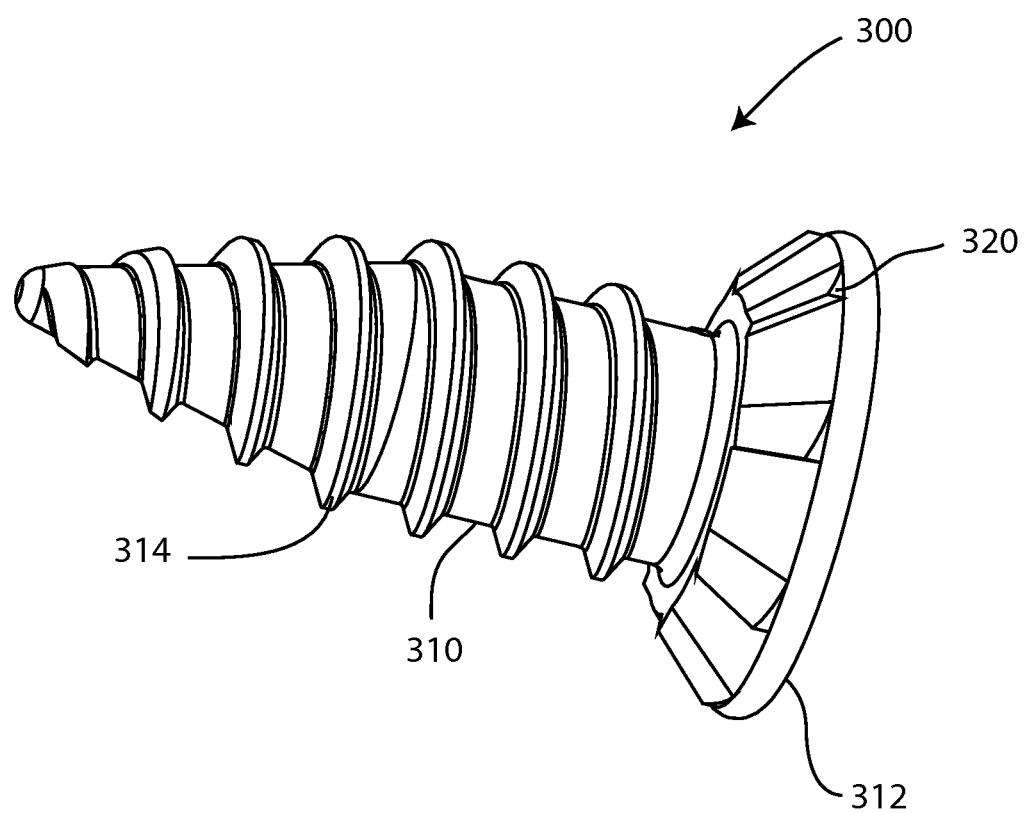
FIG. 11 is a bottom perspective view of the screw of FIG. 6.
Figure 12:
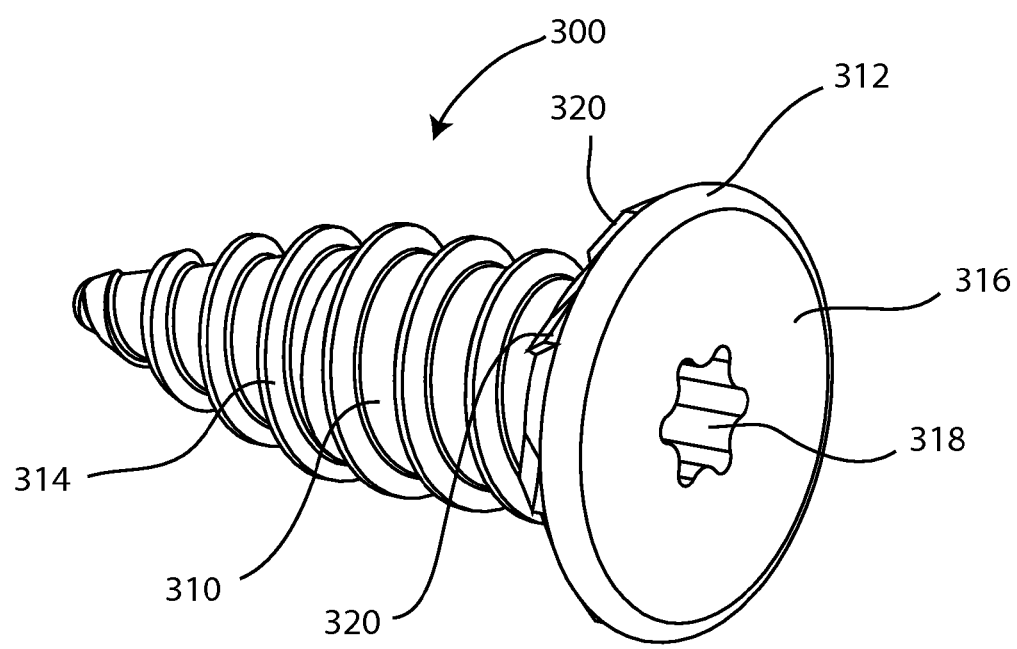
FIG. 12 is a top perspective view of the screw of FIG. 6.

Referring to FIGS. 7A and 7B, the screw 300 is engaged with the sleeve 210 after one (or more) strands of the graft 3314 is (or are) projected out of the sleeve. Strands of the graft 3314 are pressed between the sleeve body 310 and inside wall 212 of the sleeve 210. Additionally, at least a portion of the graft 3314 may be projecting out of the sleeve 210 and may be exposed to an outside surface of the femur 3108. In the event of the screw 300 rotating in a direction opposite to a direction in which it is turned for engagement with the sleeve, an interface created between one or more barbs 320 and the strand of the graft 3314 prevents or otherwise inhibits it from rotating in the opposite direction, thereby resulting in an anti-back-out feature of the screw 300.

Figure 13A:
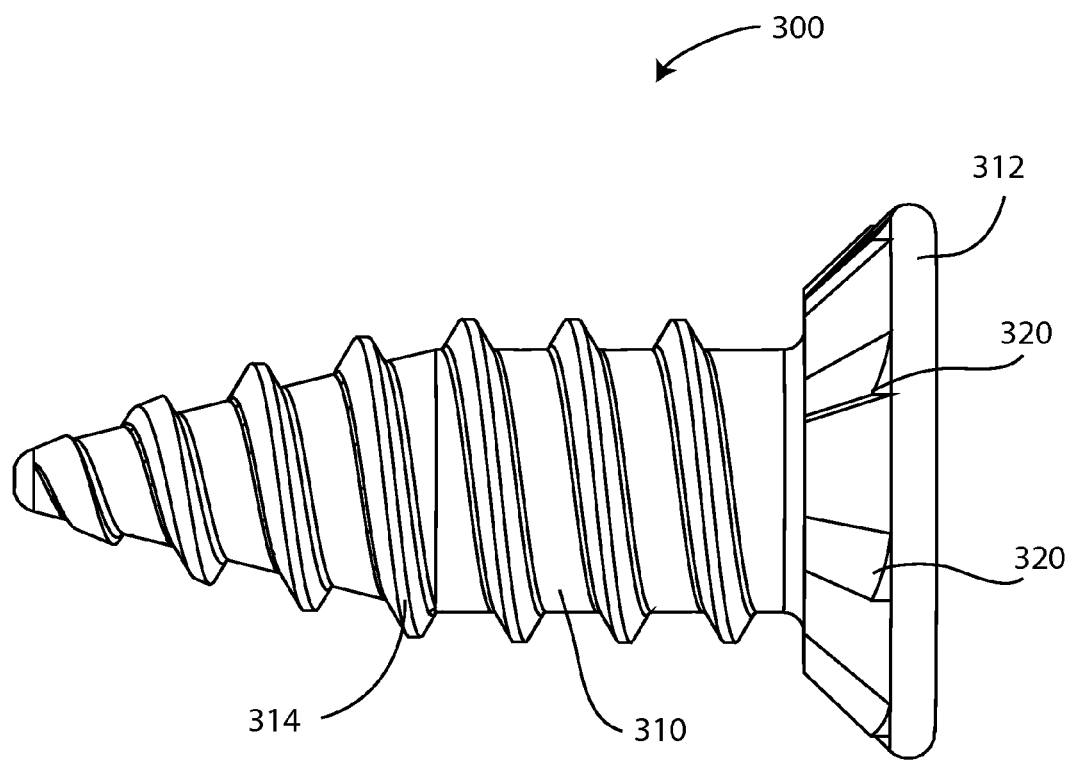
FIG. 13A is a side view of the screw of FIG. 6.
Figure 13B:
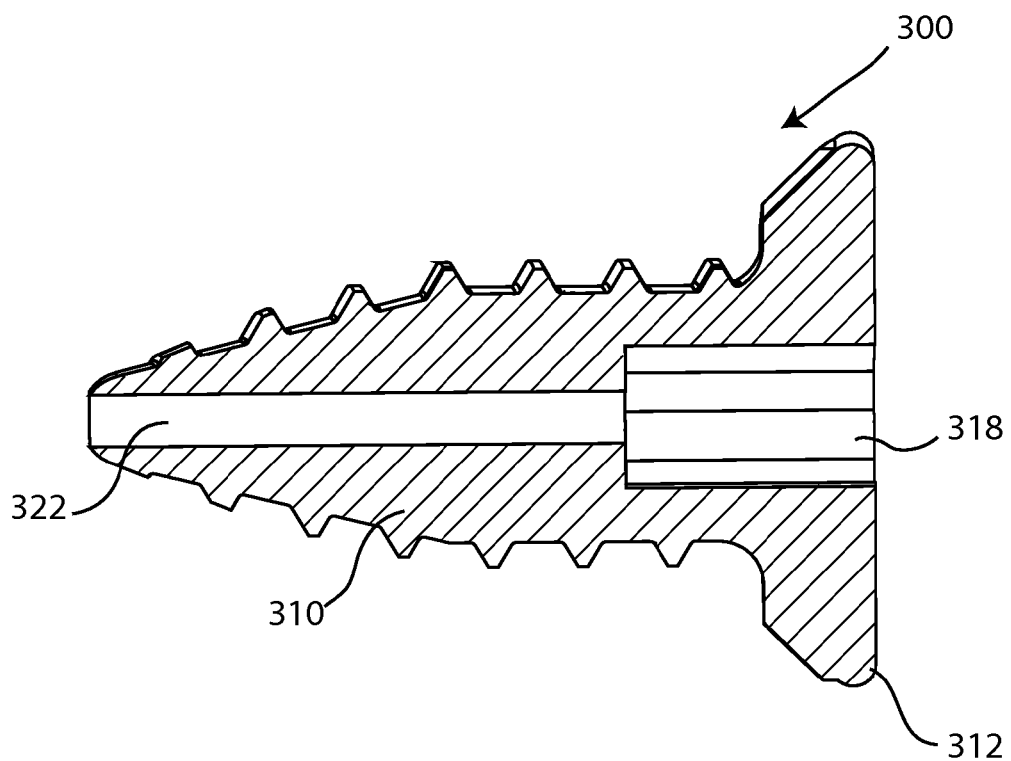
FIG. 13B is a cross-sectional side view of the screw of FIG. 6.

Referring to FIG. 13B, the screw 300 may further be cannulated with a cannula 322 passing from the central void 318 to the distal end of the screw 300. The cannula 322 may allow passage of a guide wire or other means to direct the screw 300 to its appropriate position.

Figure 14:
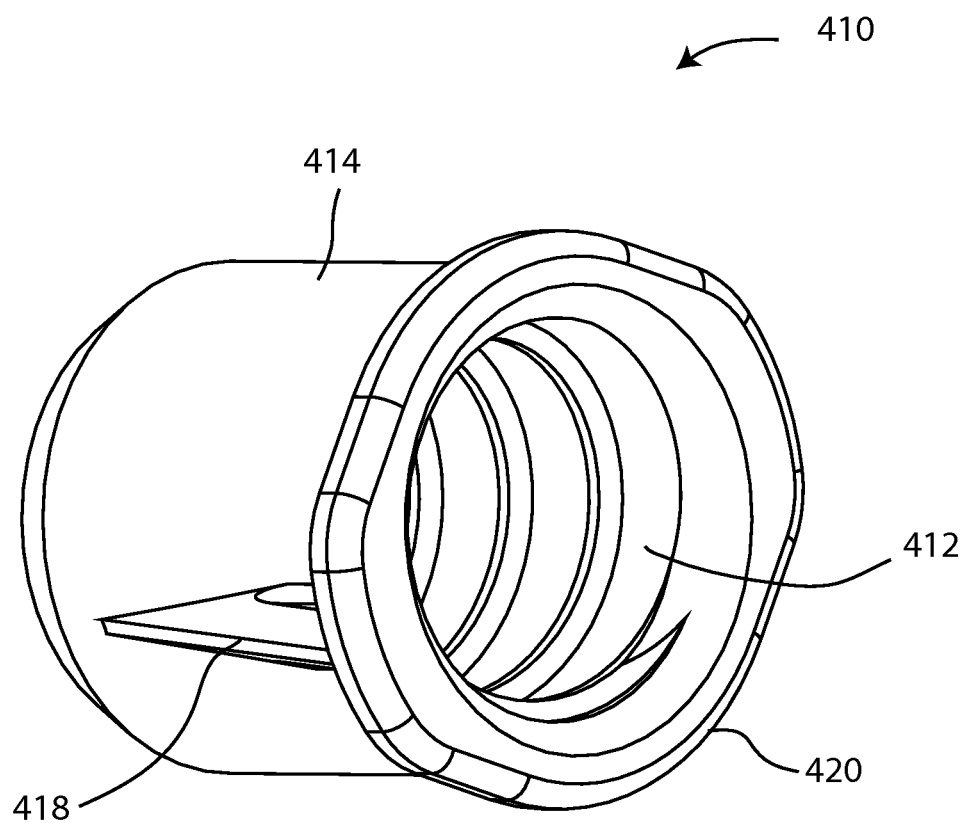
FIG. 14 is a perspective view of an alternate embodiment sleeve with a lip.
Figure 15:
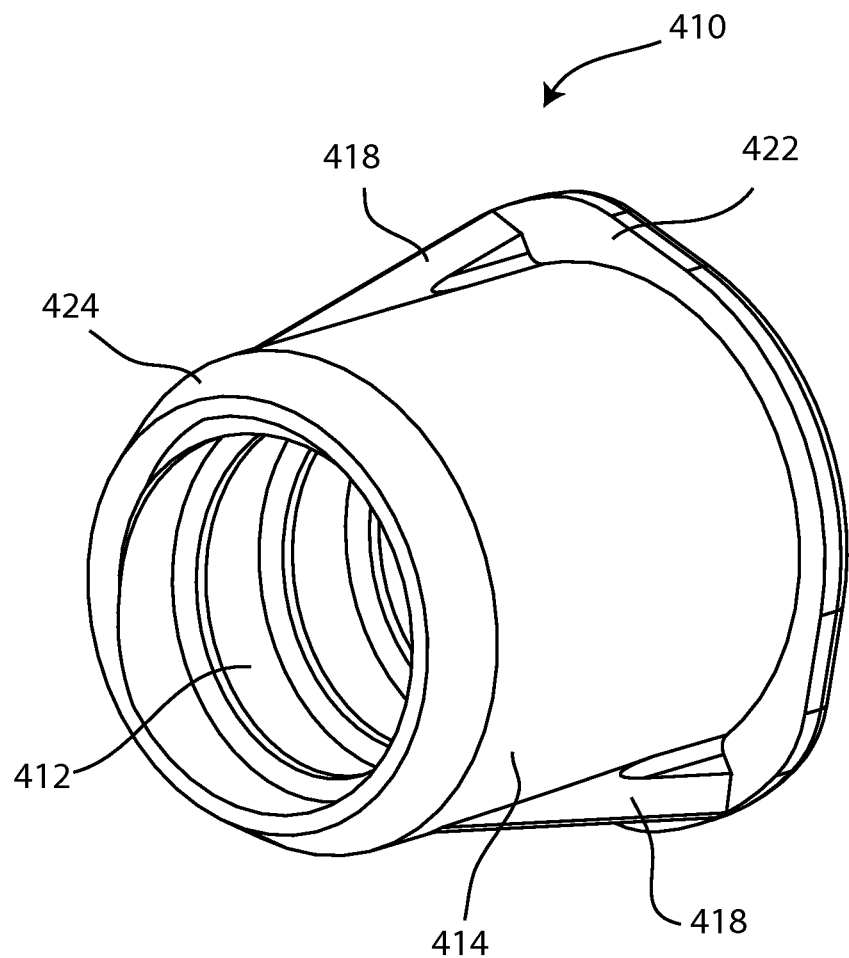
FIG. 15 is a bottom perspective view of the sleeve of FIG. 14.
Figure 16:
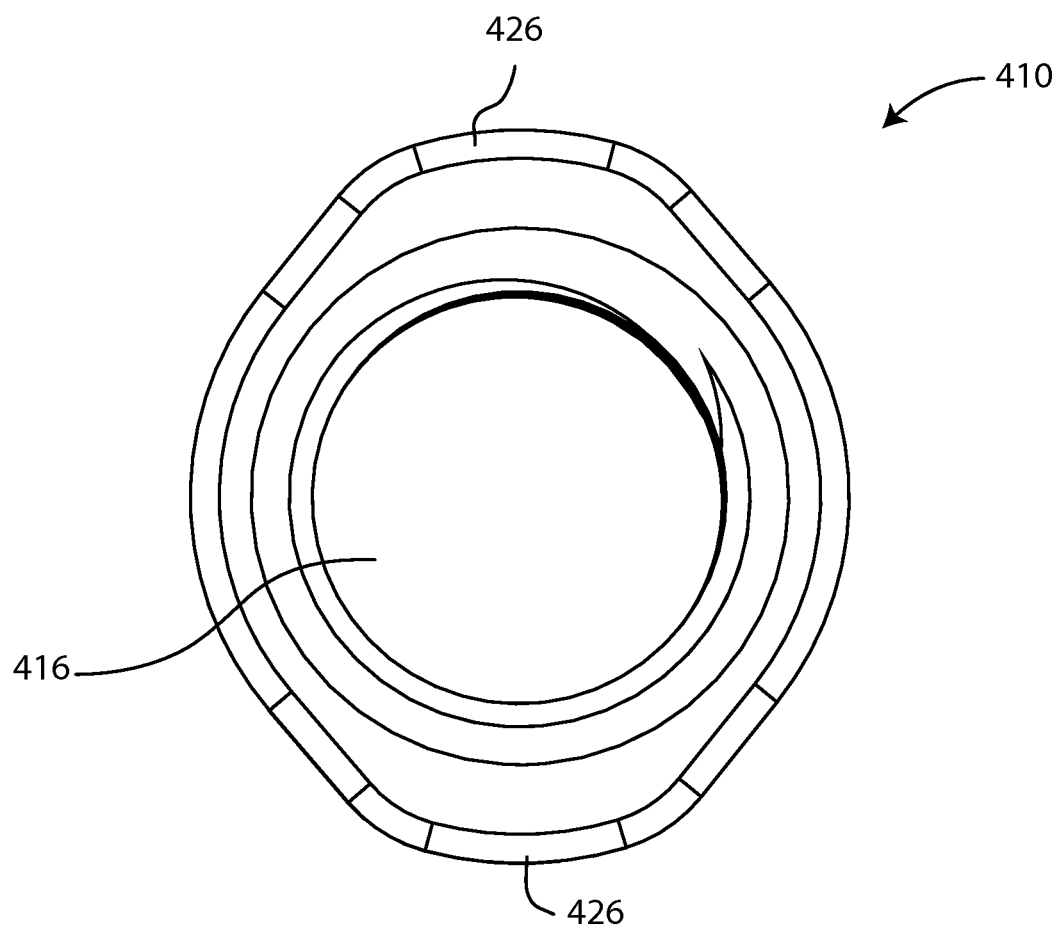
FIG. 16 is a top view of the sleeve of FIG. 14.

Referring to FIGS. 14-16, an alternate embodiment of a sleeve 410 is illustrated. The sleeve 410 similarly includes an inside wall 412, an outside wall 414 and bore 416, or tunnel, passing through a center of the sleeve 410. The sleeve 410 may also include a lip 420, or flange, on the proximal end projecting from and normal to the outside wall 414. The inside wall 412 may be threaded, with female threads, to receive a male threaded screw, which may be similar to the screw 300 previously described. However, other screws such as those depicted and described in FIGS. 21-26 may also be used. But more specifically this sleeve 410 may be more conducive to accepting a screw as depicted and described in FIGS. 25 and 26. The lip 420 may comprise a flat bottom surface 422 to engage the cortical bone to prevent the sleeve 410 from retracting entirely into the bone tunnel.

Referring to FIG. 15, the sleeve 410 may also include an anti-rotation, and anti-back out, features 418, or fins, or keels, extending both from the outside wall 414 and the bottom surface 422 of the lip 420. The fins may have a larger cross-sectional footprint toward the proximal end of the sleeve and may taper as the fins 418 extend toward a distal end until becoming flush with the outer wall 414 of the sleeve. The fins 418 may be radially positioned on opposite ends of the sleeve 410 or may be positioned in other configurations that space the fins 418 equidistant from each other; however, the fins may be staggered at odd angles. The number and spacing of the fins 418 can vary. The fins 418 may extend straight, without curving, from the bottom surface 422 of the lip 420 toward the distal end, with the fins 418 terminating and becoming flush with the outer wall 414 prior to the distal end.

This alternate embodiment sleeve 410 may include other features similar to the previous embodiment. For example, a taper 424 may extend from the distal end of the sleeve 410 wherein the circumference is relatively smaller than the main body of the sleeve 410. The fins 418 may extend into the taper 424 and become flush with the taper 424, the fins terminating at the taper 424.

Referring to FIG. 16, the lip 420 may include radial bulges 426 to create a larger footprint for the sleeve 410 to engage the cortical bone. The bulges 426 may be radially opposed and evenly spaced; however, the number of bulges and spacing of each may vary.

Figure 17:
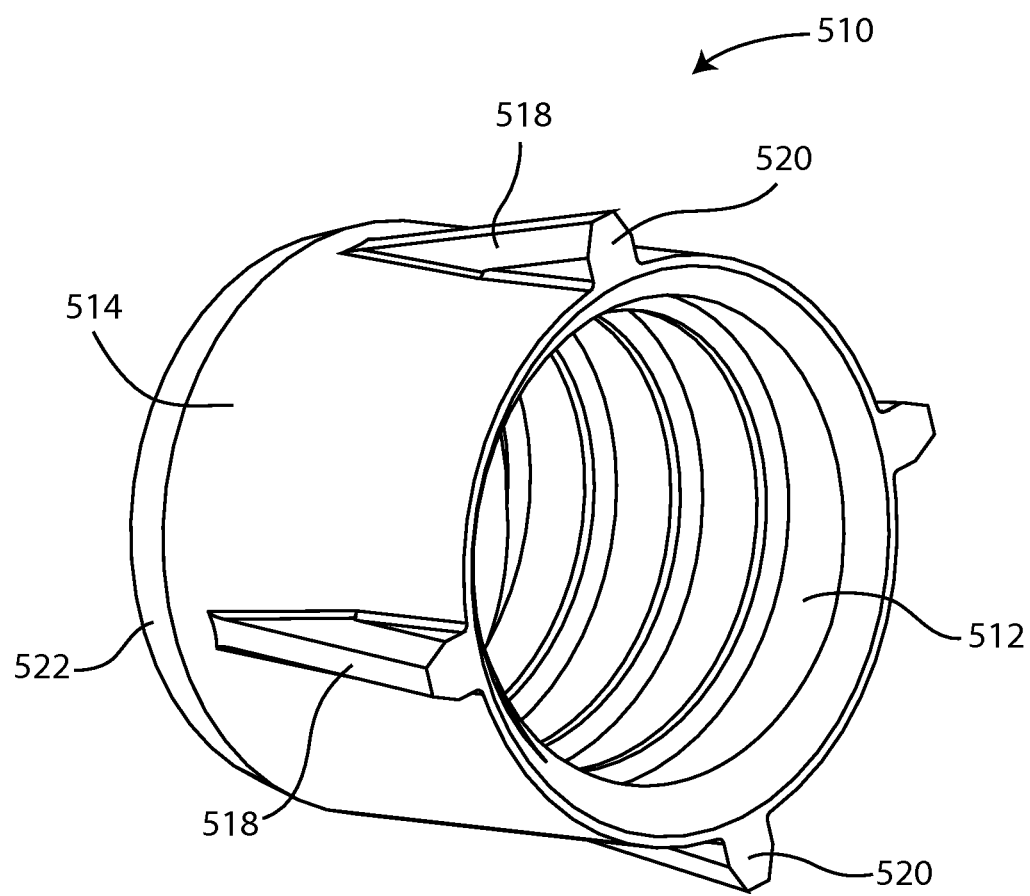
FIG. 17 is a perspective view of an alternate embodiment sleeve with a plurality of keels.
Figure 18:
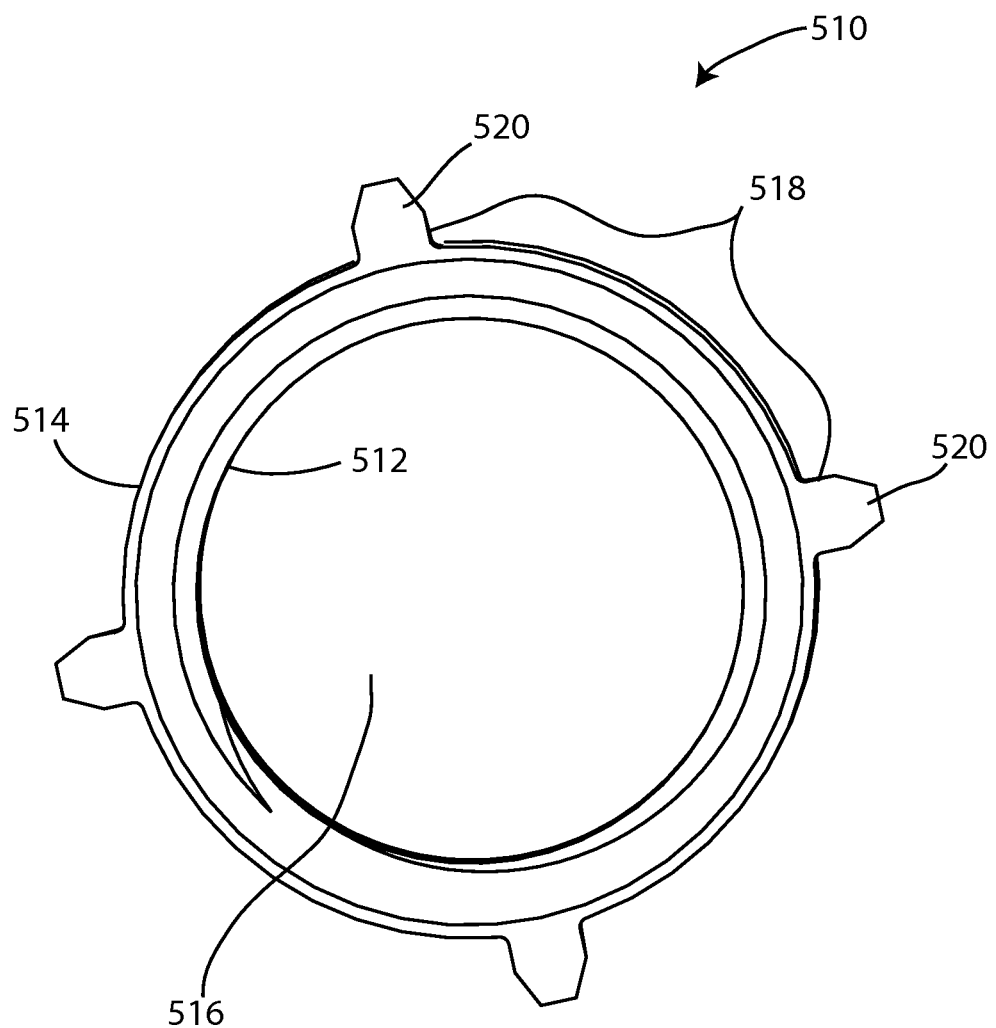
FIG. 18 is a top view of the sleeve of FIG. 17.

Referring to FIGS. 17 and 18, an alternate embodiment of a sleeve is illustrated. The sleeve 510, similar to previous embodiments, includes an inner wall 512, an outer wall 514 and a bore 516, or tunnel, longitudinally passing through the center of the sleeve. The inner wall 512 may include threads, female threads, for engaging male threads from a screw which may be similar to screw 300, as previously described or those screws depicted and described in FIGS. 21-26 herein. But more specifically this sleeve 510 may be more conducive to accepting a screw as depicted and described in FIGS. 21 and 22.

The structure of the outer wall 514 and inner wall 512 with a tapered end 522 may be substantially similar to that of the previous sleeve 210 embodiment. However, the anti-rotation features 518, or fins, or keels, differ from the previous embodiment in that the fins 518 extend from the proximal end of the sleeve 510 wherein a flat surface 520 of the fins 518 is flush with the proximal end of the sleeve 510. The fins 518 extend toward a distal end tapering and terminating prior to the distal end and essentially becoming flush with the outer wall 514. The fins 518 are radially spaced along the outer wall 514 equidistant from one another. The number of fins, spacing and positioning may vary.

Figure 19:
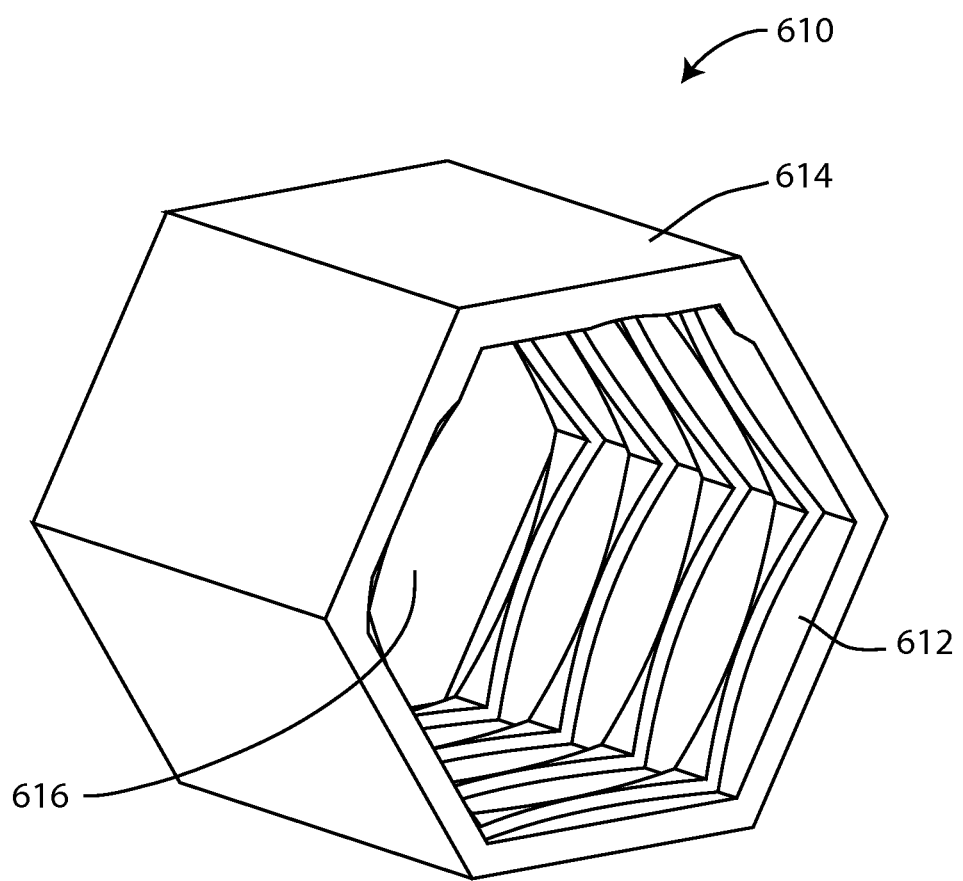
FIG. 19 is a perspective view of an alternate embodiment sleeve with a hex shaped body.
Figure 20:
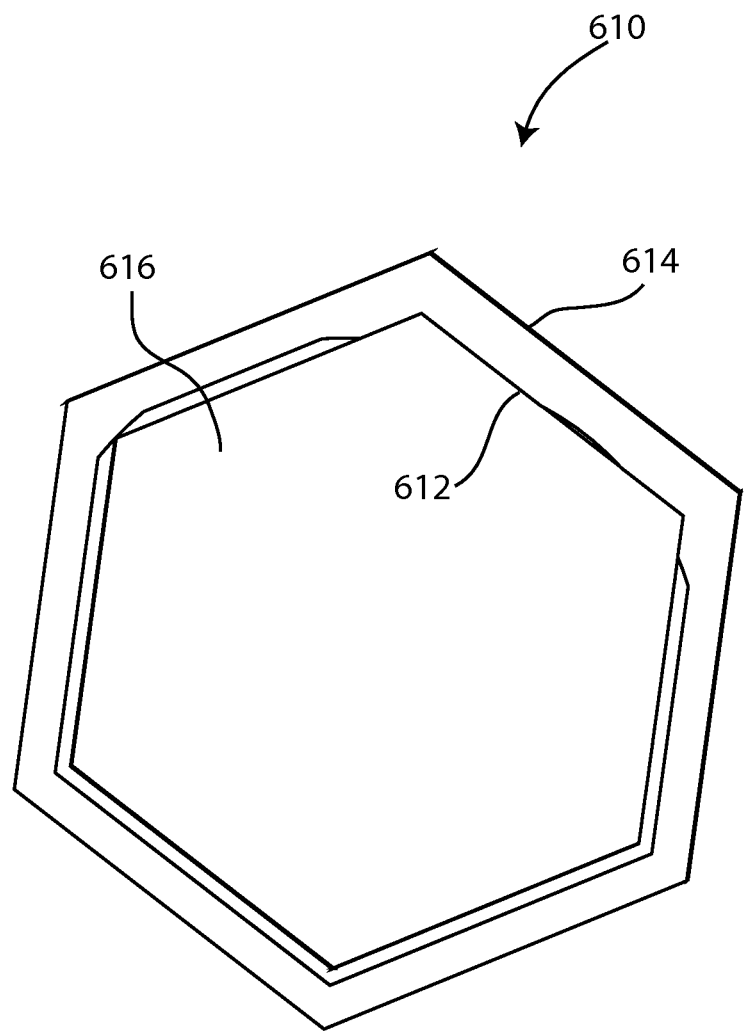
FIG. 20 is a top view of the sleeve of FIG. 19.

Referring to FIGS. 19 and 20, an alternate embodiment of a sleeve is illustrated. The sleeve 610 may be hexagonal in cross-sectional shape; however, any polygonal shape may also be used. Similar to the previous sleeve embodiments the sleeve 610 includes an inner wall 612, an outer wall 614 and a bore 616, or tunnel, longitudinally extending through the body of the sleeve 610. The shape of the sleeve provides an engaging fit within a bone tunnel as the hard angles of the hexagonal shape prevent rotation of the sleeve when a screw engages the sleeve 610. The inner wall 612 may include threads, female threads, for engaging male threads from a screw which may be similar to screw 300, as previously described or those screws depicted and described in FIGS. 21-26 herein.

Each of the sleeve embodiments may contain features from any of the other sleeve embodiments. Alternate features have been contemplated such as the threads on the inside walls of each sleeve may be replaced with ridges, a tooth or teeth or barbs or any other tractive features or means to allow the sleeve 210 to grab and capture the graft. Likewise each of the bores, passageways, central axis tunnels may have a constant diameter or taper from a proximal to a distal end or vice versa.

Figure 21:
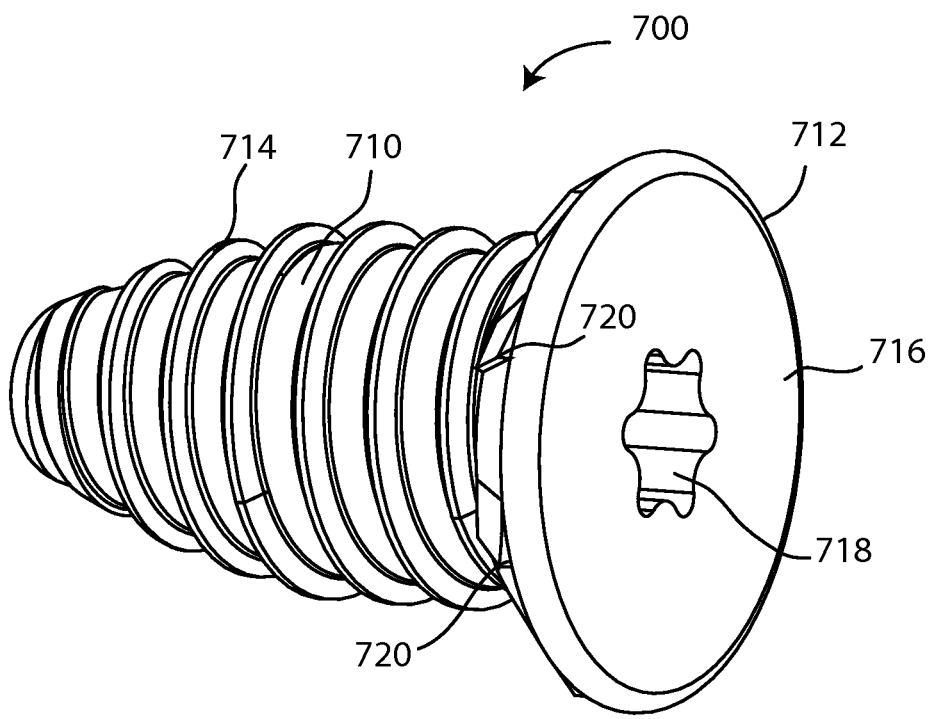
FIG. 21 is a perspective view of an alternate embodiment screw with a larger diameter body.
Figure 22:
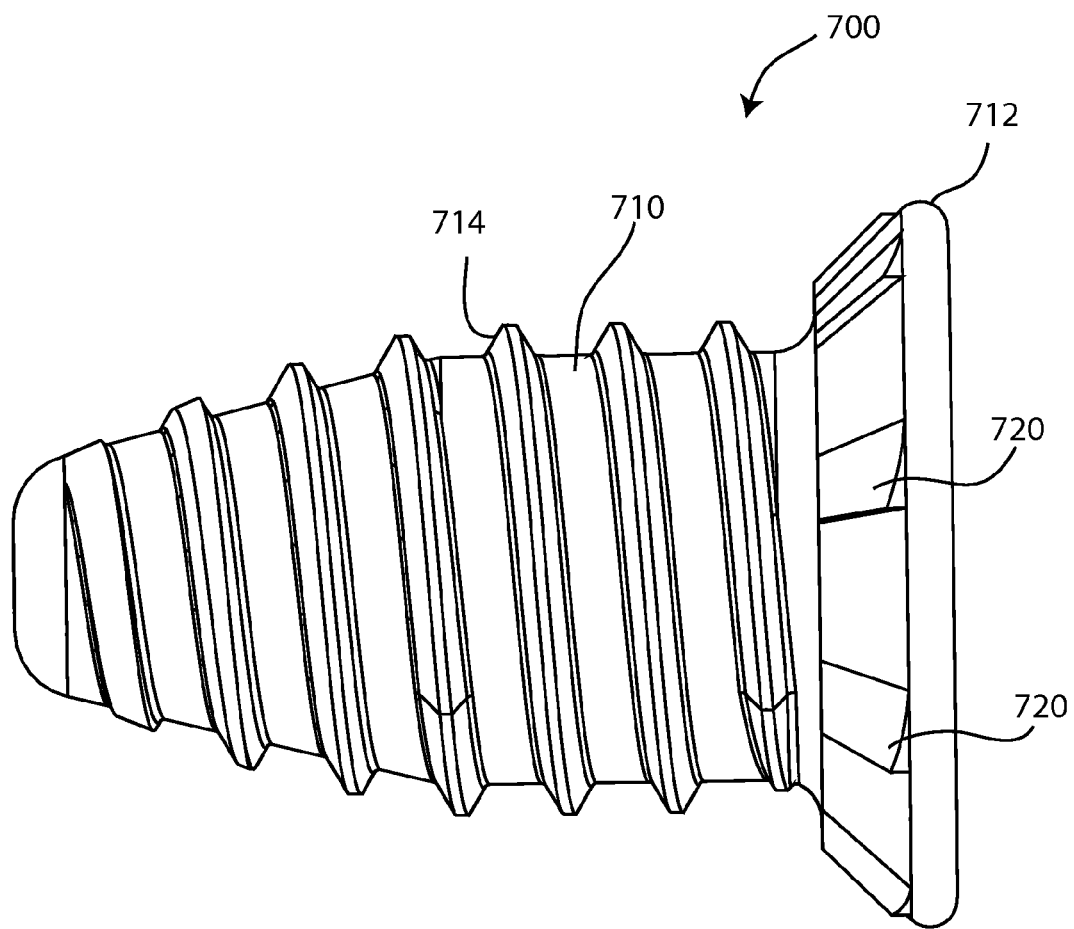
FIG. 22 is a side view of the screw of FIG. 21.

Referring to FIGS. 21 and 22, an alternate embodiment screw is illustrated. Screw 700 may be substantially similar to screw 300 provided that the diameter of a body 710 of screw 700 is larger than the diameter of body 310 of screw 300. Furthermore the transition from a head 712 of screw 700 to the body 710 may be less abrupt because of the larger diameter of the body 710 as compared to the transition from the head 312 of screw 300 to the body 310. The screw 700 includes threads 714 extending the length of the body.

The head 712 may include a flat proximal surface 716 with a central void 718, the central void 718 extending at least partially inward from the flat proximal surface 716 toward a distal end to allow access for a surgical tool. The central void 718 may be star shaped, polygonal or any other shape to allow access of and engaging of a tool for insertion of the screw 700 into the sleeve 510. However it will be appreciated that screw 700 may engage any of the previous depicted or described sleeves herein. The head 712 may have a larger diameter than the body 710 of the screw 700 wherein the diameter decreases from the head to the body creating a shoulder or lip such that the head 712 may rest against the cortex of the bone on the edge of the bone tunnel which may provide resistance to axial translation. The head 712 may also include barbs 720, or tooth or teeth positioned where the diameter is decreasing from the head 712 to the body which may also be the point where the tissue graft and the bone interface. The barbs 720 are configured in a direction to prevent the screw 700 from backing out. The screw 700 may further be cannulated in a manner similar to and described regarding the screw 300 in FIGS. 11-13B.

Figure 23:
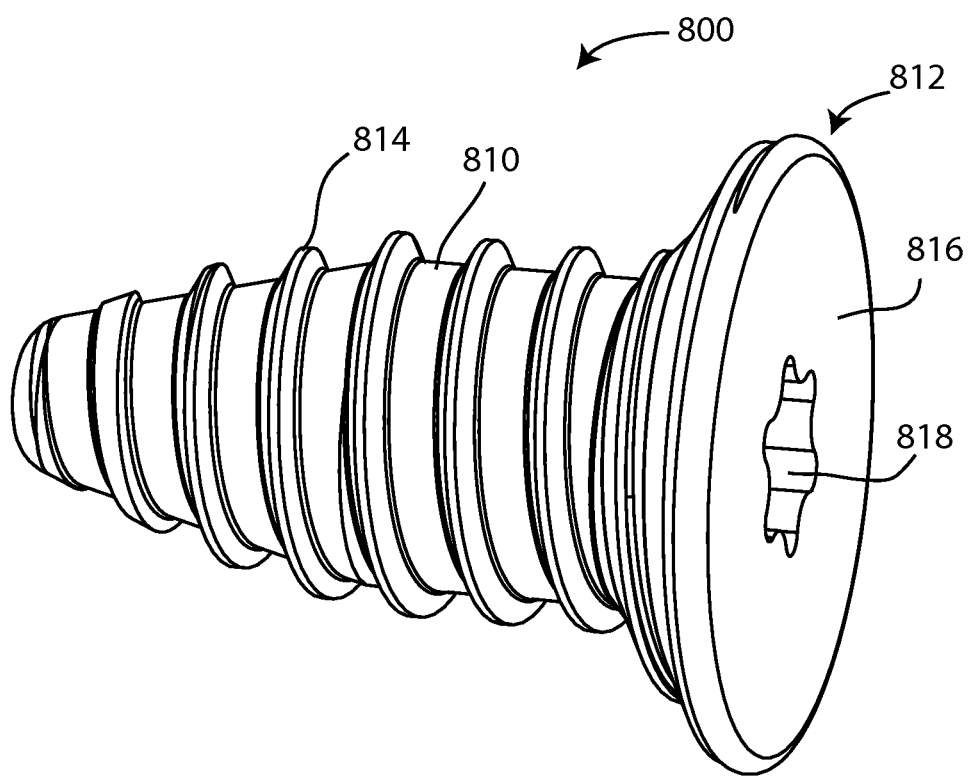
FIG. 23 is a perspective view of an alternate embodiment screw with thread extending the entire length of the body and head.
Figure 24:
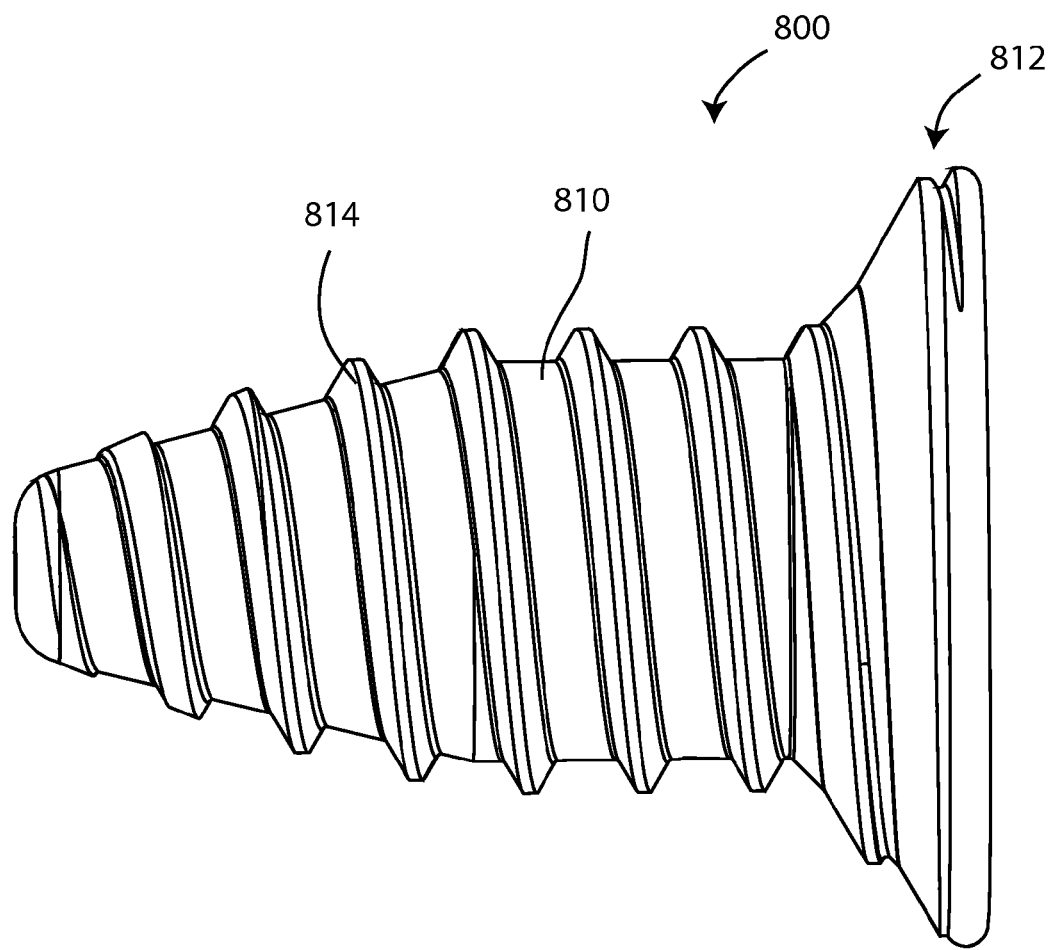
FIG. 24 is a side view of the screw of FIG. 23.

Referring to FIGS. 23 and 24, an alternate embodiment of a screw is illustrated. A screw 800 comprises a body 810 and a head with threads 814 extending from the proximal end of the head 812 to the distal end of the body 810. The head 812 may have a larger diameter than the body 810 and may taper from the distal end of the head 812 to the proximal end of the body 810. This embodiment may include features similar to previous screws in that the screw 800 may comprise a flat proximal surface 816 with a central void 818, the central void 818 extending at least partially inward from the flat proximal surface 816 toward a distal end to allow access for a surgical tool. The screw 800 may also be cannulated as similarly described with regard to previous screw embodiments. The central void 818 may be star shaped, polygonal or any other shape to allow access of and engaging of a tool for insertion of the screw 800 into the sleeve 410. Screw 800 and sleeve 410 may be ideally matched for each of the devices distinct configurations; however it will be appreciated that screw 800 may engage any of the previous depicted or described sleeves herein.

Figure 25:
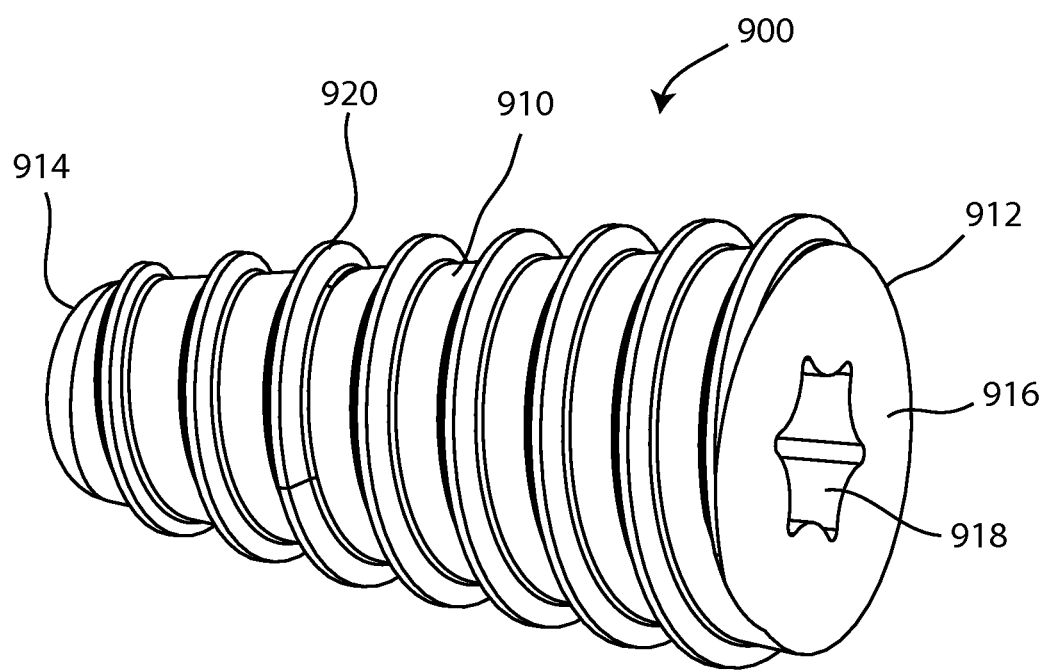
FIG. 25 is a perspective view of an alternate embodiment headless screw.
Figure 26:
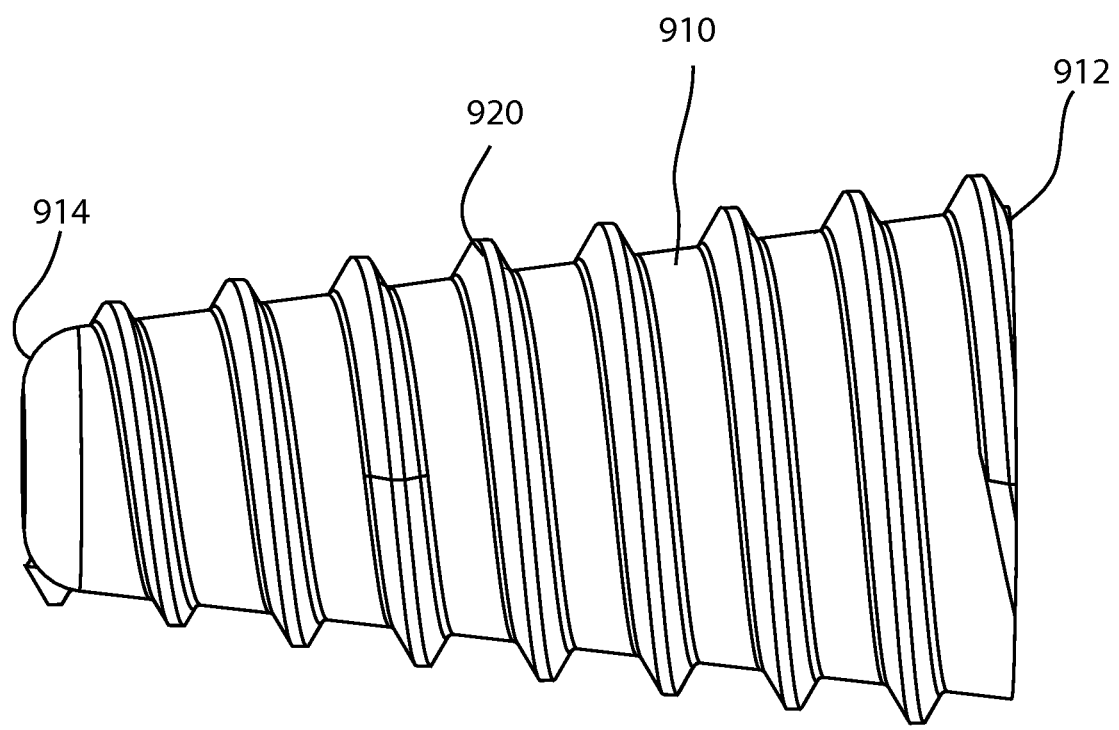
FIG. 26 is a side view of the screw of FIG. 25.

Referring to FIGS. 25 and 26, an alternate embodiment of a screw is illustrated. A screw 900 comprises a body 910 tapering from a proximal end 912 to a distal end 914 and maybe conical in shape and may have no distinct "head" of the screw 900. The screw 900 includes threads 920 extending form the proximal end 912 to the distal end 914. The proximal end 912 may comprise a flat proximal surface 916 with a central void 918, the central void 918 extending at least partially inward from the flat proximal surface 816 toward a distal end 914 to allow access for a surgical tool. The screw 900 may also be cannulated as similarly described with regard to previous screw embodiments.

Figure 29:
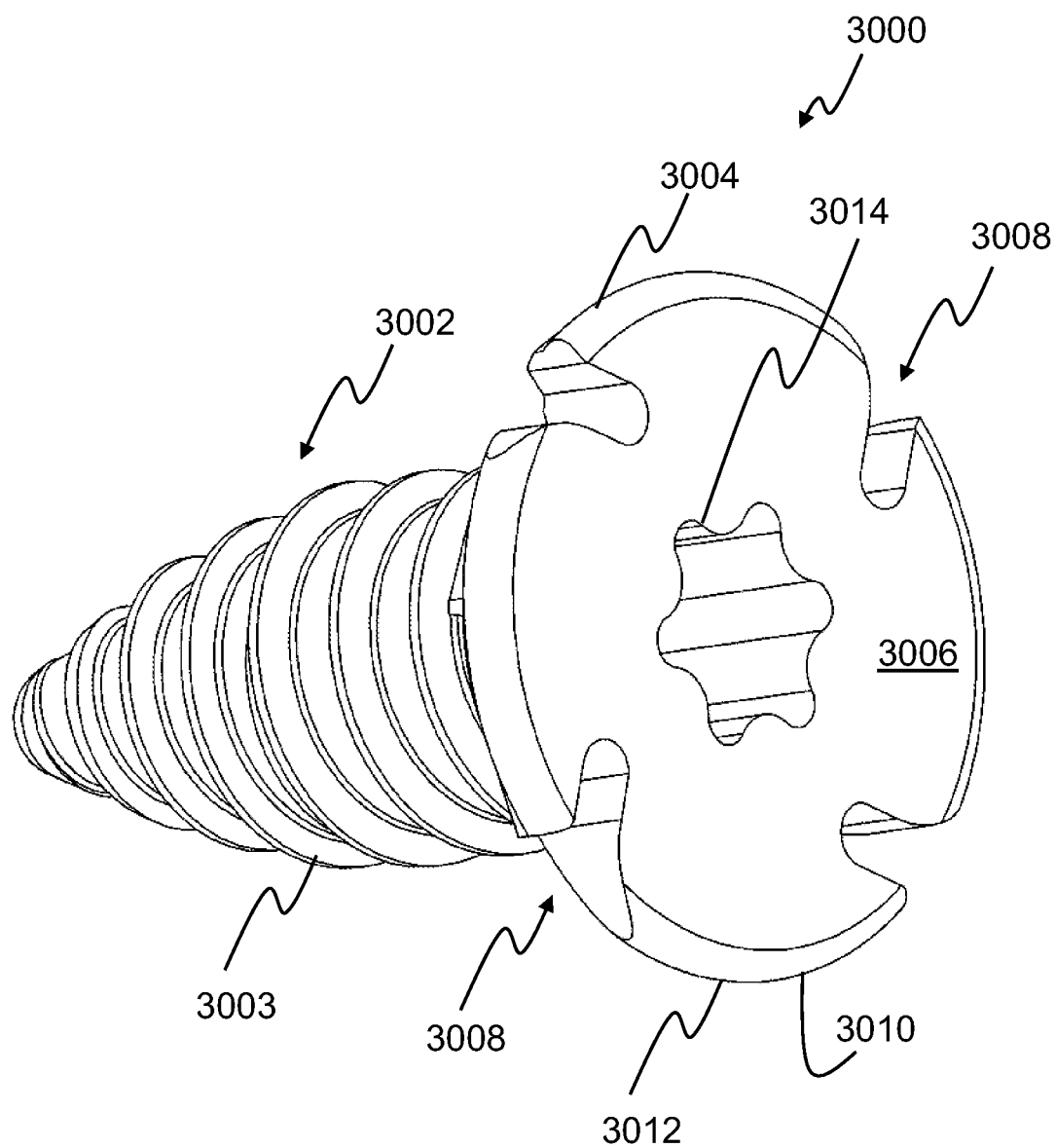
FIG. 29 is a perspective view of an alternate embodiment screw with slots.
Figure 30A:
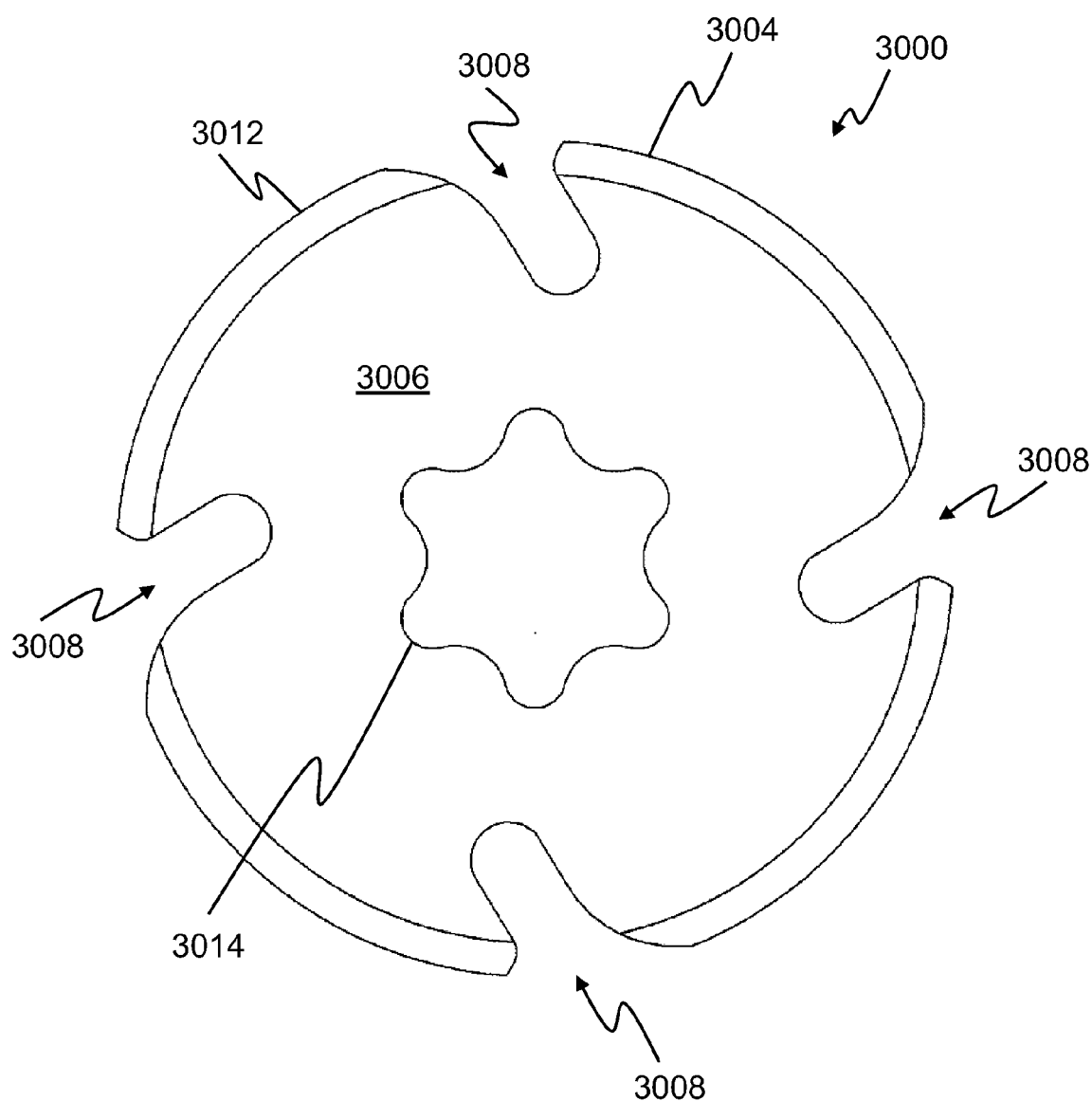
FIG. 30A is a top view of the screw of FIG. 29.
Figure 30B:
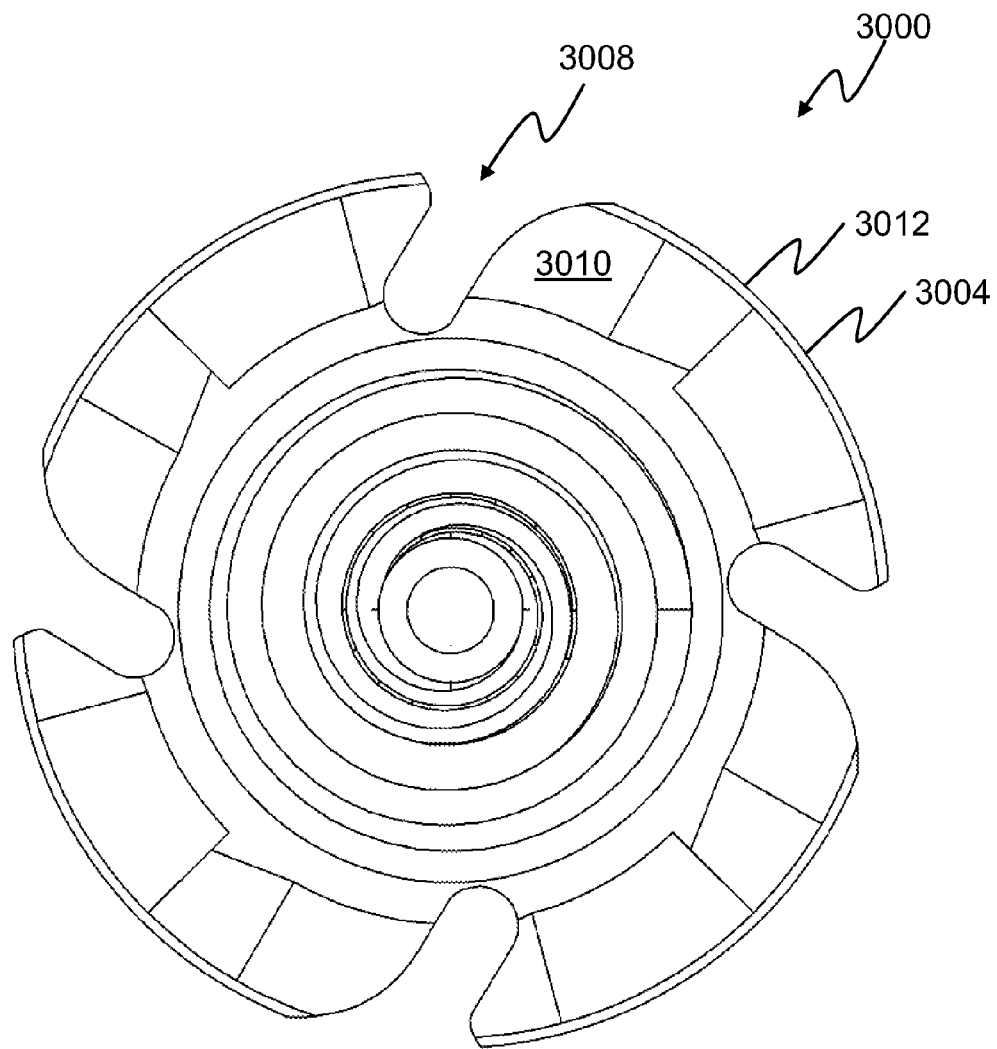
FIG. 30B is a bottom view of the screw of FIG. 29.

Referring to FIGS. 29, 30A and 30B, an alternate embodiment of a screw is illustrated. A screw 3000 includes a body 3002 and a head 3004. The body 3002 may include threads 3003, which may be male threads configured to engage the female threads of the inner wall of the sleeve. The head 3004 may include a flat proximal surface 3006 with a central void 3014, the central void 3014 extending at least partially inward from the flat proximal surface 3006 toward a distal end to allow access for a surgical tool. The head 3004 may define multiple slots 3008. Alternatively, as single slot 3008 may be defined by the head 3004. The slots 3008 extend between the flat proximal surface 3006 and a distal surface 3010 of the head 3004. The distal surface 3010 may be a surface facing the sleeve. Further, the slots 3008 extend inward from a peripheral edge 3012 of the head 3004 towards the center of the head 3004.

The slots 3008 may be aligned and extend radially inward from the outer circumference of the head 3004 towards the central void 3014, at least to some extent, in the same direction as the direction in which the screw 3008 is rotated for engagement with the sleeve. The slot 3008 may define a U, V or J shaped configuration.

Figure 31A:
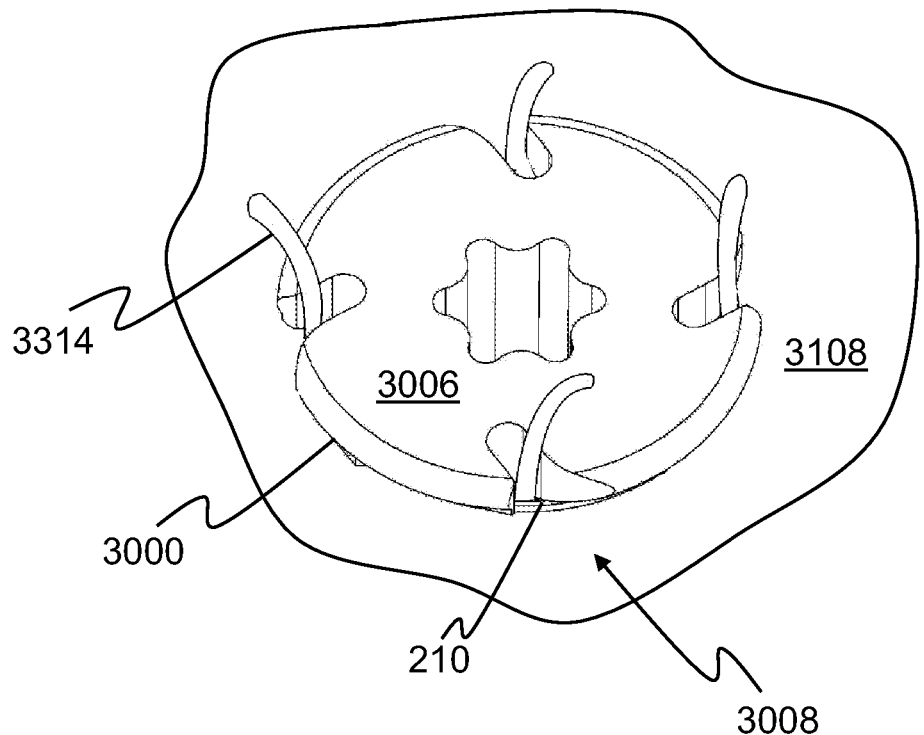
FIG. 31A is a perspective view of a graft interfacing the screw of FIG. 29.
Figure 31B:
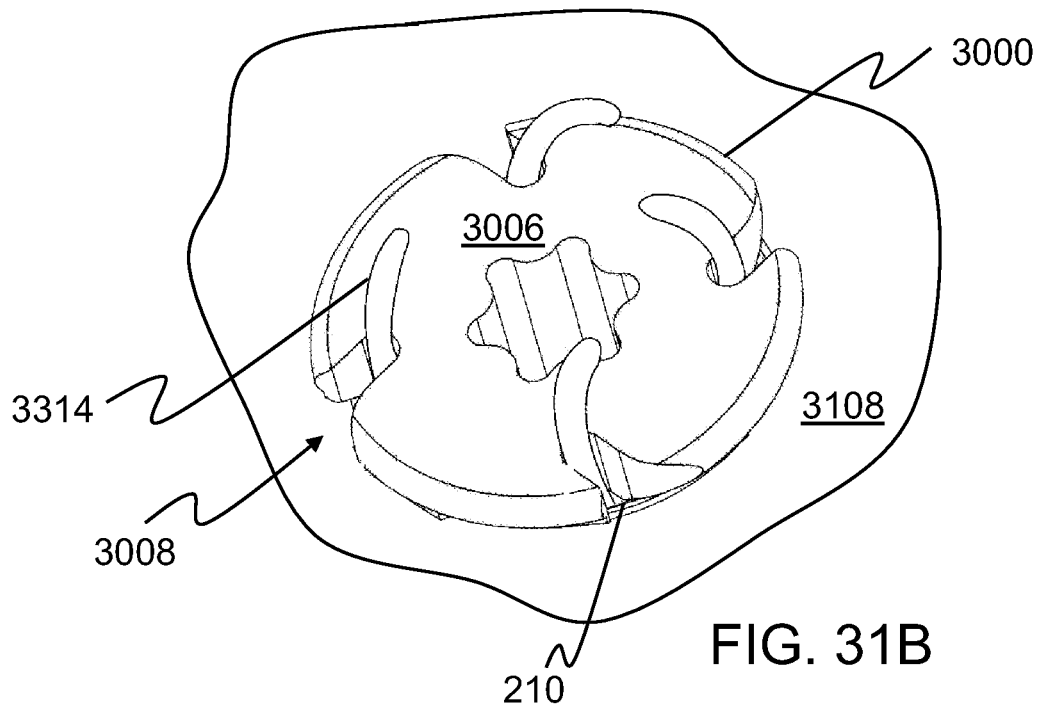
FIG. 31B is a perspective view of the graft restricting the screw of FIG. 29 from backing out.

Referring to FIGS. 31A and 31B, the slots 3008 may be aligned such that strands 3314 of the graft projecting out of the sleeve 210, and exposed to the outside surface of the femoral socket 3108, are deflected away from the center of the head 3004, thereby preventing the strand 3314 from being caught in the slots 3008, when the screw 3000 is being engaged with the sleeve 210. On the other hand, if the screw 3000 attempts to rotate in the opposite direction, the strands 3314 of the graft may be caught in the slots 3008, thereby preventing the screw 3000 from backing out. FIG. 31A illustrates the strands of the graft 3314 being deflected away from being caught in the slots 3008, when the screw 3000 is rotated in an engagement direction, for engaging the screw 3000 with the sleeve 210. FIG. 31B illustrates the strands 3314 of the graft being caught in the slots 3008, when the screw 3000 is rotated in a direction which is opposite to the engagement direction, thereby preventing the screw 3000 from backing out. Even if the strands 3314 of the graft were to be trimmed to prevent the strands 3314 from projecting above the proximal surface 3006 of the screw 3000, the interface between the remaining portions of the strands 3314 located within at least a portion of one or more of the slots 3008 may still prevent the screw 3000 from backing out.

Figure 32A:
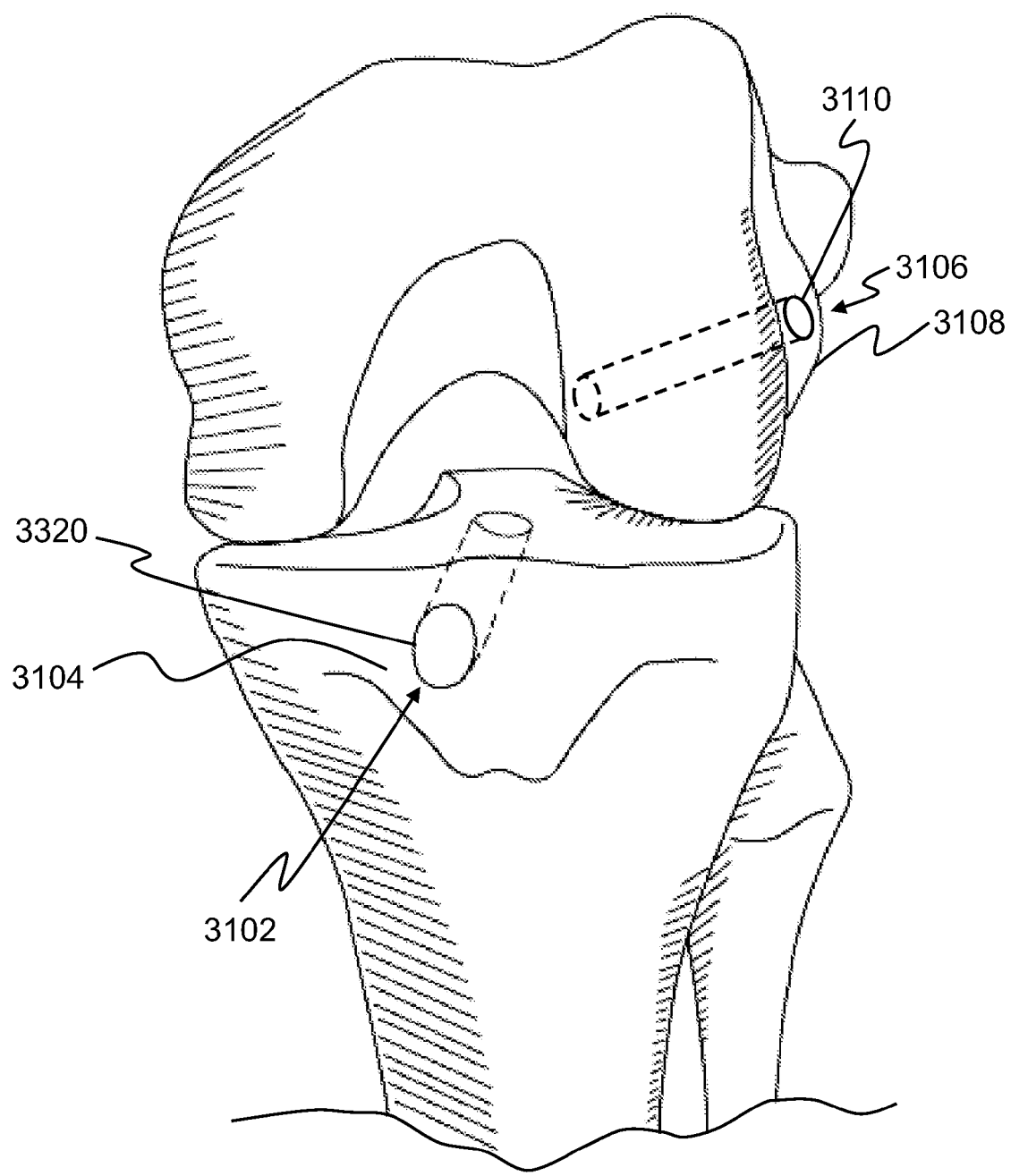
FIG. 32A is a perspective view of a first tunnel created in a tibial socket.
Figure 32B:
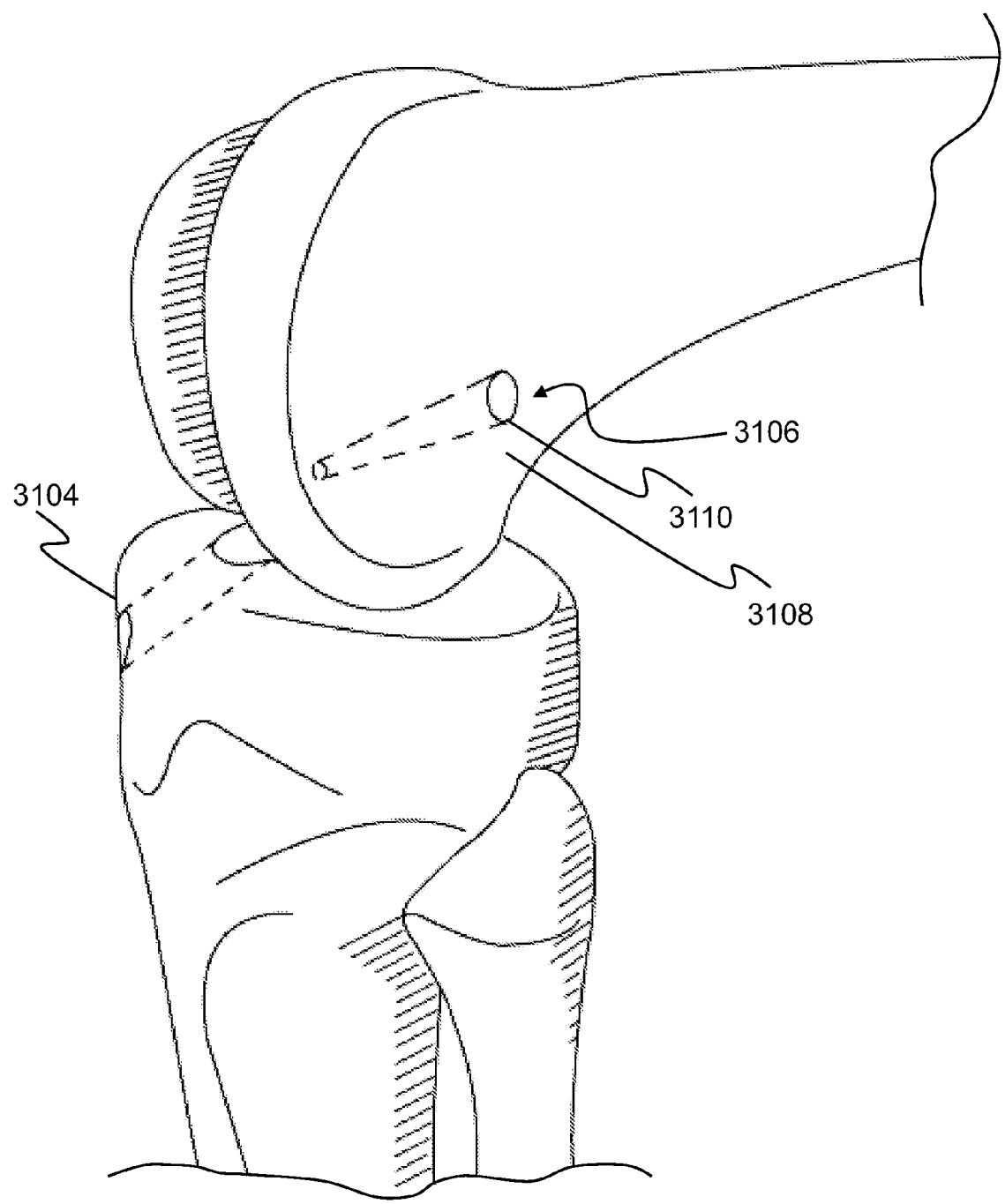
FIG. 32B is a perspective view of a second tunnel created in a femoral socket.
Figure 32C:
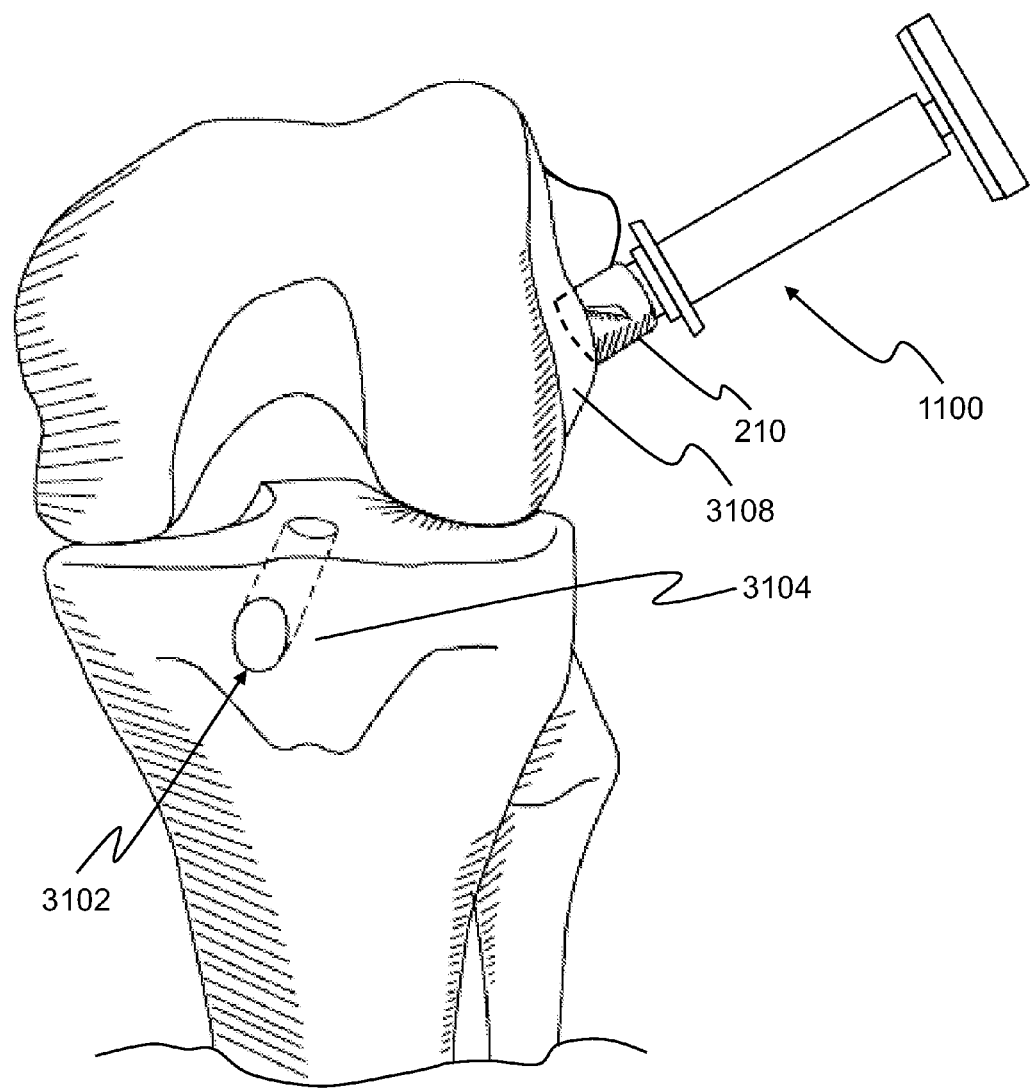
FIG. 32C is a perspective view of a sleeve being engaged with the femoral socket of FIG. 32B.
Figure 32D:
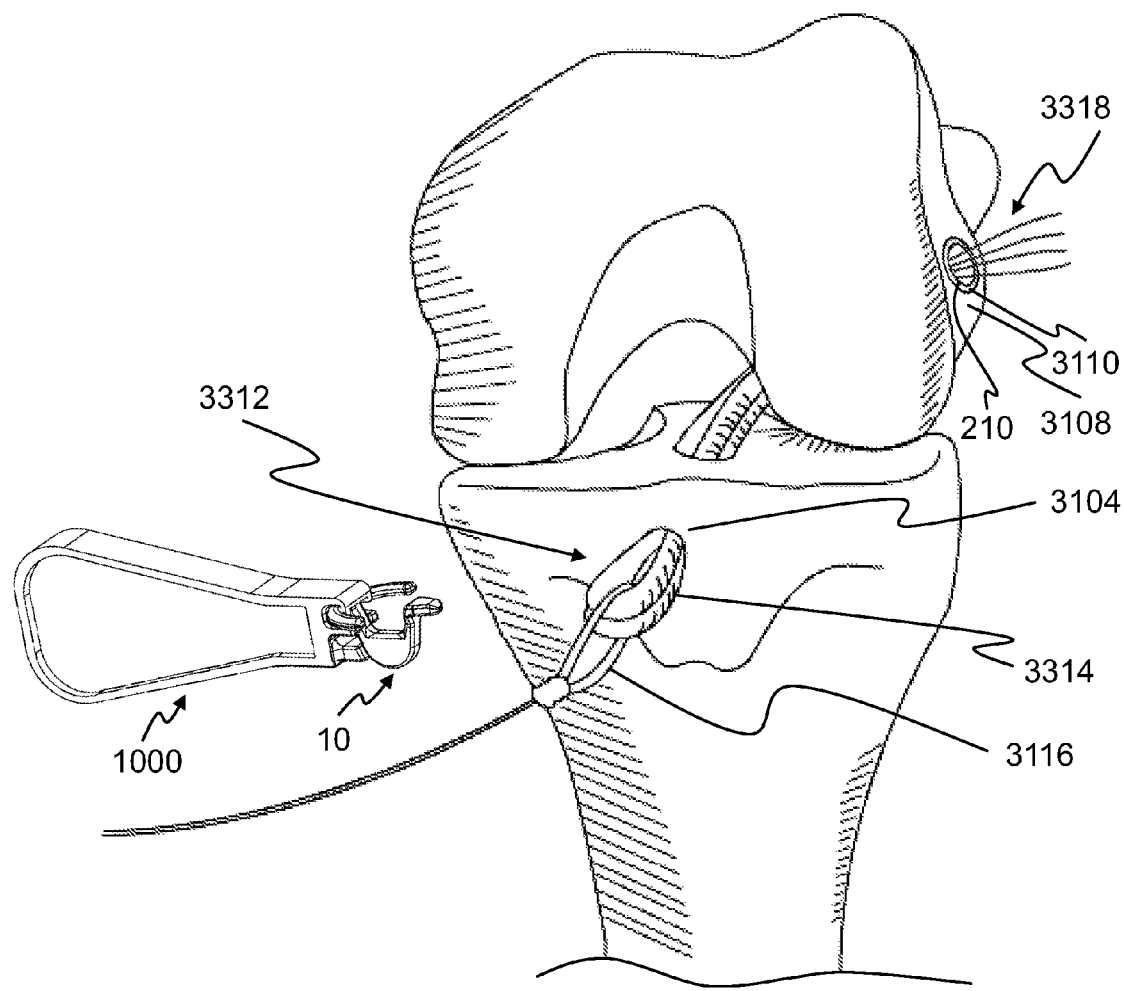
FIG. 32D is a perspective view of a graft being passed through the first and second tunnel of FIGS. 32A and 32B.
Figure 32E:
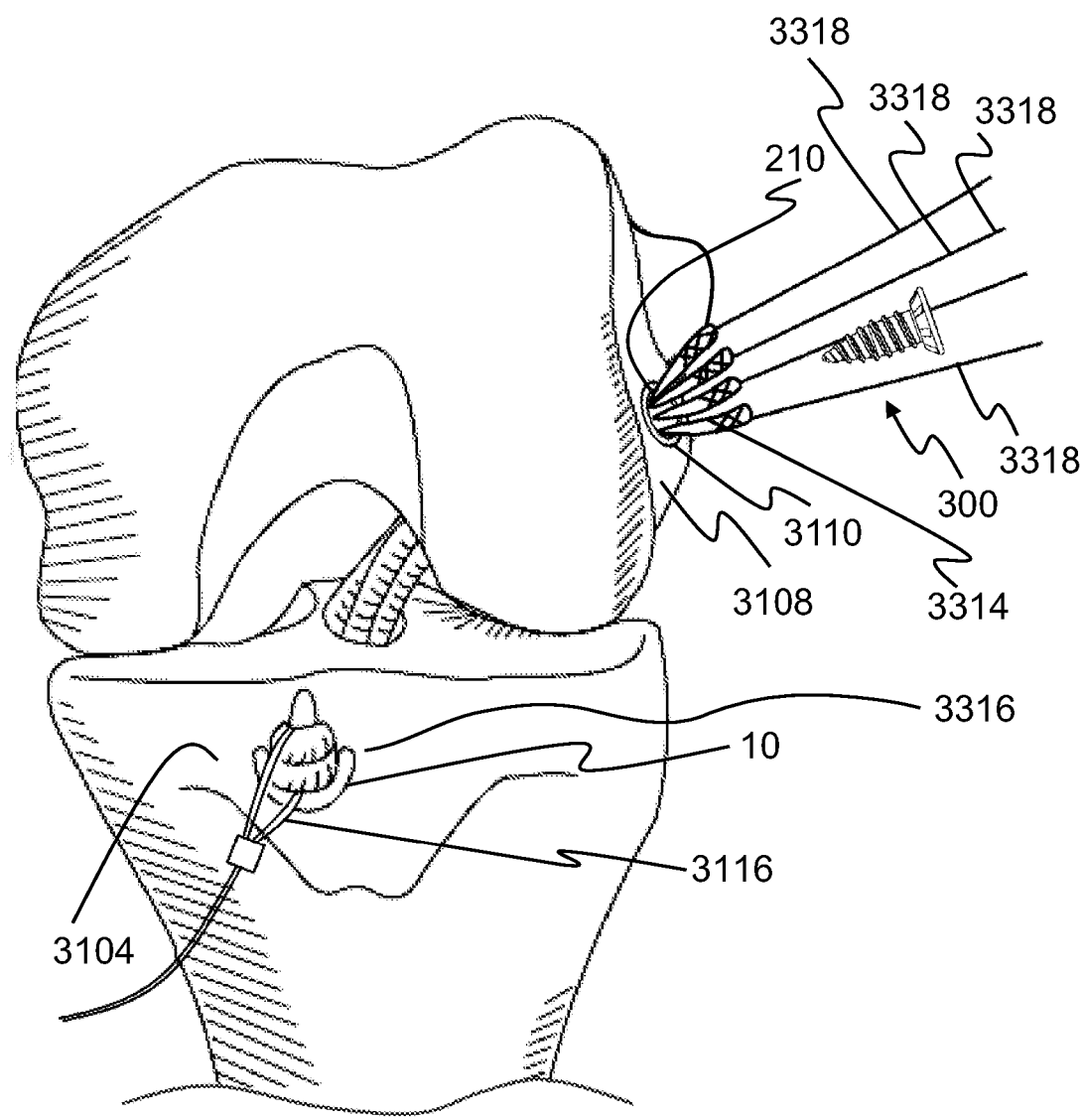
FIGS. 32E and 32F are perspective views of the body of FIG. 1 being engaged with the graft, and the screw of FIG. 11 being engaged with the sleeve.
Figure 32F:
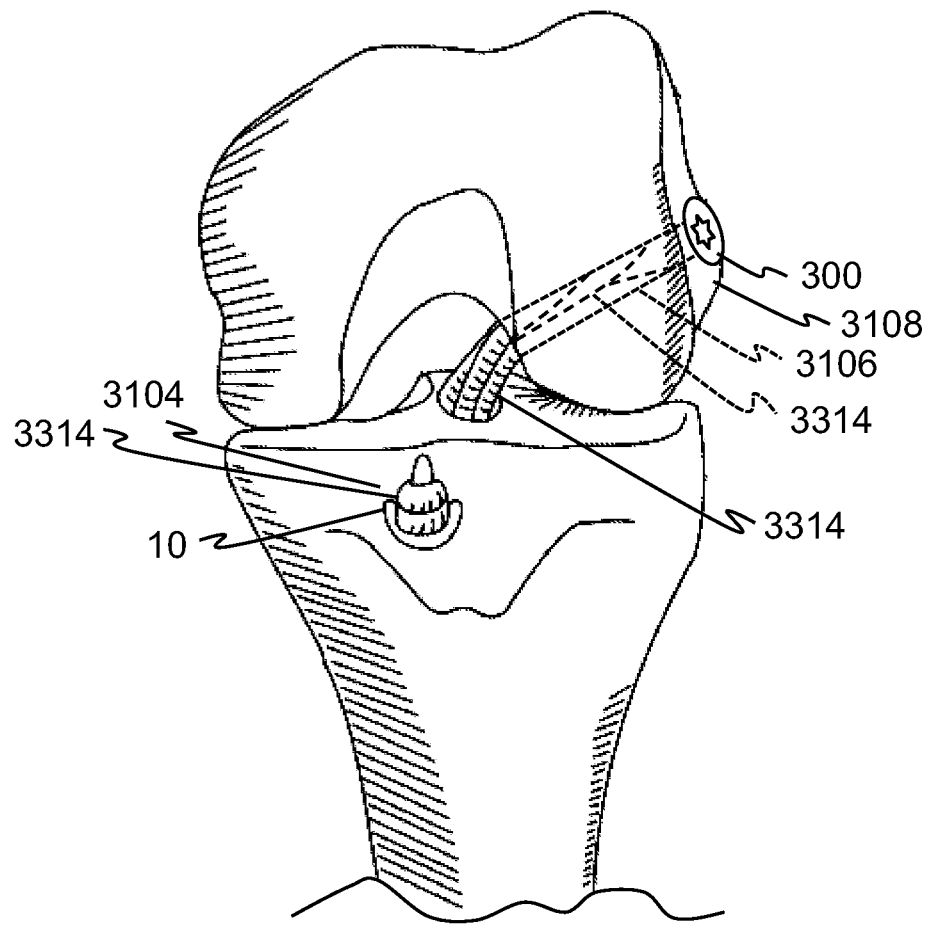
Figure 33:
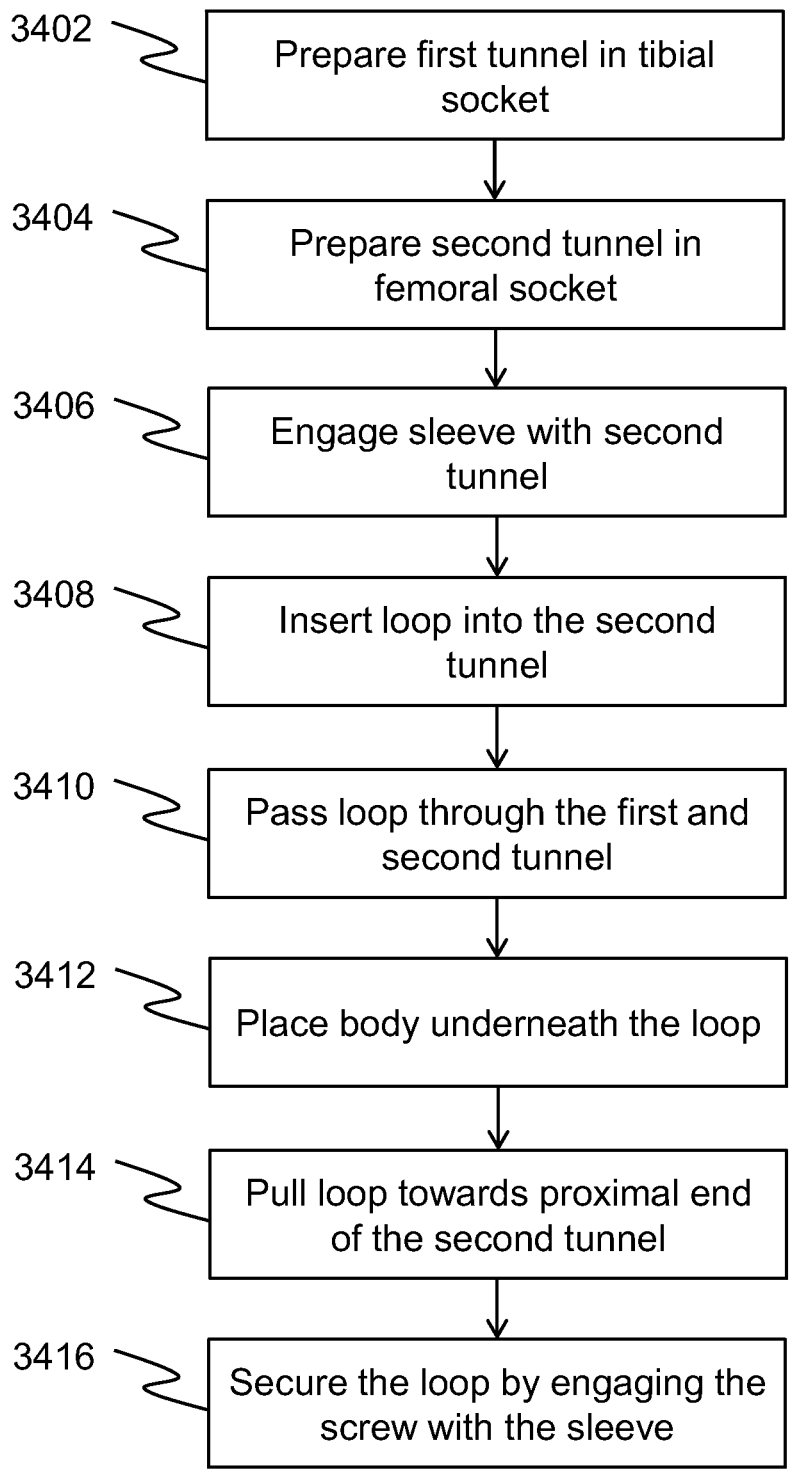
FIG. 33 is a flow chart of a method of ACL reconstruction.

Referring to FIGS. 32A-33, application of the system to ACL graft reconstruction is discussed. A first tunnel 3102 is prepared in a tibial socket 3104 (step 3402), which may be referred to as a first member. A second tunnel 3106 is prepared in a femoral socket 3108 (step 3404), which may be referred to as second member. The second tunnel 3106 is reamed at a proximal end 3110 for receiving the sleeve 210 and the screw 300. It shall be noted that, if the screw 300 is intended to be engaged with the wall of the second tunnel 3106, apart from being engaged with the sleeve 210, then threads may be created on the wall of the second tunnel 3106. The treads on the wall of the second tunnel 3106 may be created while reaming the second tunnel 3106.

The sleeve 210 is engaged with the second tunnel 3106 at the proximal end 3106 of the second tunnel 3106 (step 3406). The sleeve 210 may be engaged using an insertion tool 1100 illustrated in FIG. 28. The insertion tool 110 may define threads at one end, which may correspond to the threads of the sleeve 210. The sleeve 210 is engaged with the insertion tool 1100 at the threaded portion of the insertion tool 1100. Thereafter, the sleeve 210 along with the insertion tool 1100 is aligned along the axis of the second tunnel 3106. The distal end of the sleeve 210 is aligned with the proximal end 3110 of second tunnel 3106. Subsequently, force, such as by hammering, driving, screwing, twisting, or otherwise advancing, is applied over the head of the tool 1100, thereby pushing and/or rotating the sleeve 210 into the second tunnel 3106. As the sleeve 210 is pushed into the second tunnel 3106, the fins provided in the sleeve 210 cut through the wall of the second tunnel 3106. The sleeve 210 is firmly held in the second tunnel 3106 due to a friction fit, between the surface of the sleeve 210 and the wall of the second tunnel 3106, and between fins of the sleeve 210 and the bone. The fins also prevent the sleeve 210 from rotating when the screw 300 is engaged with the sleeve 210.

Further, a loop 3312 formed using a graft 3314 is inserted into the proximal end 3110 of the second tunnel 3106. A suture 3116 may be engaged at a portion of the loop 3312 where the graft bends to form the loop 3312. An implement may be engaged with the suture 3116, which may enable the loop to be passed through the second tunnel 3106 and then through the first tunnel 3102. Further, a set of suture 3318 may be engaged with the free ends of the graft 3314.

After the sleeve 104 is engaged with the second tunnel 3106, the loop 3312 is inserted into the second tunnel 3106 (step 3408), with the bent portion of the loop 3312 facing the second tunnel 3106. The loop 3312 is passed through the tunnels 3106, 3102, such that the portion of the graft 3314 that first entered the second tunnel 3106 is accessible outside the proximal end 3320 of the first tunnel (step 3410). The free ends of the graft 3314 may extend out of the proximal end 3110 of second tunnel 3106.

Thereafter, the at least a portion of the body 10 (in one example, the second flange 14 and retention portion 16) is placed underneath the loop 3312 (step 3412) using an installation instrument 1000, if desired. The suture 3116 is removed from the loop 3312. Subsequently, the loop 3312 is pulled towards the proximal end 3110 of second tunnel 3106 until further movement of the graft 3314 is restricted by the flanges of the body 10 (step 3414). The screw 300 is then engaged with the sleeve 210 (step 3416). The engagement of the screw 300 and the sleeve 210 results in securing the free ends of the graft 3314 at the proximal end 3110 of second tunnel 3106. Excess graft projecting over the head of the screw 310 may be trimmed or otherwise secured.

In the screw and sleeve systems in each instance there may be clearance between the inner walls of the sleeves and the screws to allow the graft to pass through the sleeve and still engage the screw. It is appreciated that various features of the above-described examples can be mixed and matched to form a variety of other combinations and alternatives. The systems described herein need not be limited to ACL graft fixation or sports medicine and knee surgical applications and may be used in instances for alternative functions, including, but not limited to other soft tissue to bone fixation.

Figure 28:
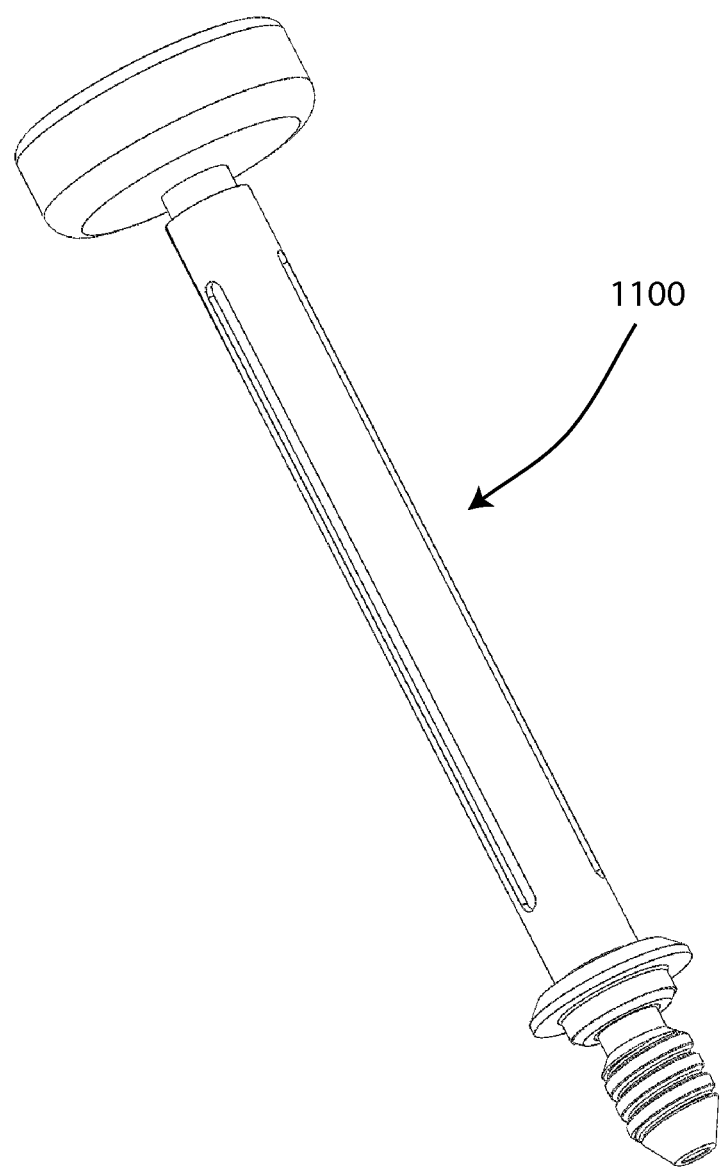
FIG. 28 is a perspective view of an installation instrument for use with the screw and sleeve of FIGS. 7 and 8.

Referring to FIG. 28, an insertion tool 1100 may be used to install both the sleeve and screw within the bone tunnel. The tool may be malleted or otherwise forced to drive the sleeve into place and also include a screw interface to engage the central void of the screw to insert the screw within the sleeve.

The components, screws, sleeves and devices disclosed herein may be made from metals, polymers, ceramics, glasses, composite materials, biological materials or tissues, or other biocompatible materials. Different materials may be used for individual components. Different materials may be combined in a single component.

It should be understood that the present system, screw, sleeves, apparatuses, and methods are not intended to be limited to the particular forms disclosed; rather, they are to cover all combinations, modifications, equivalents, and alternatives.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

The present invention may be embodied in other specific forms without departing from its spirit or essential characteristics. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system for fixing a flexible member between a first member of a patient and a second member of the patient, comprising:
   a body comprising:
   a retention portion, wherein the retention portion engages the flexible member and is received in a first tunnel defined by the first member; and
   a first flange coupled to the retention portion, wherein the first flange engages an outside surface of the first member, wherein the first flange comprises an arm that extends along a circular path and terminates in a free end; and a screw that at least partially secures at least one strand of the flexible member near a proximal end of a second tunnel defined by the second member.

2. The system of claim 1, wherein the body further comprises a first leg and a second leg, wherein the first leg and the second leg extend from the retention portion, wherein the first flange extends from the first leg, wherein the first leg couples the first flange to the retention portion.

3. The system of claim 2, further comprising a second flange, wherein the second flange extends from the second leg, wherein the second leg couples the second flange to the retention portion opposite the first flange.

4. The system of claim 1, further comprising a second flange coupled to the retention portion opposite the first flange, wherein the second flange engages the outside surface of the first member.

5. The system of claim 1, wherein the screw comprises a head comprising at least one tooth, wherein the tooth forms an interface with the flexible member, wherein the interface prevents the screw from rotating in a removal direction which is opposite to an engagement direction in which the screw is rotated to secure the at least one strand of the flexible member to the second member.

6. The system of claim 1, further comprising a sleeve, wherein the sleeve is received in the second tunnel, and wherein the screw is engaged within the sleeve.

7. The system of claim 1, further comprising a sleeve, wherein the sleeve comprises at least one fin, wherein the fin projects from an outside surface of the sleeve.

8. The system of claim 7, wherein the fin tapers to become flush with the sleeve as the fin advances toward a distal end of the sleeve.

9. The system of claim 1, wherein the first flange comprises an outer profile that is continuously convex.

10. A method for fixing a flexible member between a first member of a patient and a second member of the patient, the method comprising:
 engaging the flexible member with a retention portion of a body;
 tensioning the flexible member, wherein the tensioning results in receiving at least the retention portion of the body inside a first tunnel defined by the first member;
 limiting the body from being completely received by the first tunnel as a result of the tensioning, by engaging at least a first flange with an outside surface of the first member, wherein the first flange comprises an arm that extends along a circular path and terminates in a free end; and
 at least partially securing at least one strand of the flexible member near a proximal end of a second tunnel defined by the second member.

11. The method of claim 10, wherein engaging the flexible member with the retention portion comprises accommodating at least one loop formed by the flexible member in the retention portion.

12. The method of claim 10, wherein limiting the body from being completely received by the first tunnel comprises engaging at least a second flange with the outside surface of the first member.

13. The method of claim 10, wherein securing the at least one strand of the flexible member comprises pressing the at least one strand of the flexible member against an outside surface of the second member.

14. The method of claim 10, wherein securing the at least one strand of the flexible member comprises:
 engaging a screw with the second tunnel through which the at least one strand protrudes; and
 creating an interface between a head of the screw and the at least one strand, such that the interface prevents the screw from rotating in a removal direction which is opposite to an engagement direction in which the screw is rotated to engage the screw with the second tunnel.

15. The method of claim 10, wherein securing the at least one strand of the flexible member comprises pressing the at least one strand against an inside surface of a sleeve, wherein the sleeve is at least partially located inside the second tunnel.

16. A system for fixing a flexible member between a first member of a patient and a second member of the patient, comprising:
 a body comprising:
 a retention means for engaging the flexible member; and
 an engagement means for engaging the body with an outside surface of the first member, wherein the engagement means comprises an arm that extends along a circular path and terminates in a free end; and
 a securing means for securing at least one strand of the flexible member against a wall of a tunnel.

17. The system of claim 16, wherein the retention means is received into the first member.

18. The system of claim 16, wherein the securing means creates an interface with the at least one strand, such that the interface prevents the securing means from rotating in a removal direction which is opposite to an engagement direction in which the securing means is rotated to secure the at least one strand of the flexible member against the wall of the tunnel.

19. The system of claim 18, further comprising an accommodation means, wherein the accommodation means receives at least one strand of the flexible member and the securing means.

20. The system of claim 16, wherein the arm comprises an outer profile that is continuously convex.

* * * * *